US008957771B2

(12) United States Patent
Arringdale et al.

(10) Patent No.: US 8,957,771 B2
(45) Date of Patent: Feb. 17, 2015

(54) APPARATUS, SYSTEM, AND METHOD FOR IMPLEMENTING AND MONITORING BREATH ALCOHOL TESTING PROGRAMS, USUALLY FROM A FIXED POINT LOCATION, SUCH AS A HOME

(75) Inventors: David L. Arringdale, Ankeny, IA (US); Michael W. Walter, Urbandale, IA (US); Douglas E. DeVries, Johnston, IA (US)

(73) Assignee: Consumer Safety Technology, Inc., Clive, IA (US)

( * ) Notice: Subject to any disclaimer, the term of this patent is extended or adjusted under 35 U.S.C. 154(b) by 343 days.

(21) Appl. No.: 13/221,995

(22) Filed: Aug. 31, 2011

(65) Prior Publication Data

US 2011/0309932 A1     Dec. 22, 2011

Related U.S. Application Data

(63) Continuation-in-part of application No. 12/973,550, filed on Dec. 20, 2010, which is a continuation of application No. 12/504,714, filed on Jul. 17, 2009, now Pat. No. 7,934,577.

(60) Provisional application No. 61/081,594, filed on Jul. 17, 2008.

(51) Int. Cl.
*B60Q 1/00*     (2006.01)
*B60K 28/06*     (2006.01)
*G01N 33/497*     (2006.01)

(52) U.S. Cl.
CPC .......... *B60K 28/063* (2013.01); *B60W 2540/24* (2013.01); *G01N 33/4972* (2013.01)
USPC ............................ 340/439; 180/272; 340/576

(58) Field of Classification Search
USPC ...................... 180/272; 340/439, 539.25, 576
See application file for complete search history.

(56) References Cited

U.S. PATENT DOCUMENTS

| | | | |
|---|---|---|---|
| 4,487,055 A | 12/1984 | Wolf | |
| 4,678,057 A | 7/1987 | Elfman et al. | |
| 4,738,333 A | 4/1988 | Collier et al. | |
| 4,809,810 A | 3/1989 | Elfman et al. | |
| 4,902,628 A * | 2/1990 | Blair | 436/132 |
| 4,926,164 A * | 5/1990 | Porter et al. | 340/576 |
| 5,393,495 A | 2/1995 | Forrester | |
| 5,400,637 A | 3/1995 | Forrester | |
| 5,426,415 A * | 6/1995 | Prachar et al. | 340/576 |
| 6,026,674 A | 2/2000 | Gammenthaler | |
| 6,167,746 B1 | 1/2001 | Gammenthaler | |
| 6,229,908 B1 | 5/2001 | Edmonds, III et al. | |
| 6,313,791 B1 * | 11/2001 | Klanke | 342/357.75 |
| 6,358,384 B1 | 3/2002 | Warburton | |

(Continued)

OTHER PUBLICATIONS

Search Report for co-pending PCT/US2009/051007 by the International Searching Authority.

*Primary Examiner* — Brent Swarthout
(74) *Attorney, Agent, or Firm* — McKee, Voorhees & Sease

(57) ABSTRACT

The invention relates to devices, systems and methods for thwarting attempts to circumvent breath alcohol level testing and monitoring programs. In-home monitoring systems as well as ignition interlock systems are described. Accelerometers and/or compasses are used to detect movement of the device. GPS and image data are collected at the time samples are collected to verify their authenticity. A system is provided for use by a third party service provider to provide reports and notification to monitoring authorities.

24 Claims, 16 Drawing Sheets

(56) References Cited

U.S. PATENT DOCUMENTS

| | | |
|---|---|---|
| 6,405,728 B1 | 6/2002 | Van Hall et al. |
| 6,445,178 B1 * | 9/2002 | Hoekstra .................. 324/207.12 |
| 6,726,636 B2 | 4/2004 | Der Ghazarian et al. |
| 6,748,792 B1 * | 6/2004 | Freund et al. .................. 73/23.3 |
| 6,792,793 B2 | 9/2004 | Mendoza |
| 6,853,956 B2 | 2/2005 | Ballard, Jr. et al. |
| 6,870,475 B2 | 3/2005 | Fitch et al. |
| 6,962,153 B2 | 11/2005 | Gershteyn |
| 7,171,842 B2 | 2/2007 | Stock et al. |
| 7,204,335 B2 | 4/2007 | Stewart et al. |
| 7,218,236 B2 | 5/2007 | Mobley et al. |
| 7,256,700 B1 | 8/2007 | Ruocco et al. |
| 7,287,617 B2 | 10/2007 | Mobley et al. |
| 7,299,890 B2 | 11/2007 | Mobley et al. |
| 7,329,390 B2 | 2/2008 | Stock et al. |
| 7,400,258 B2 | 7/2008 | Crespo |
| 7,413,047 B2 * | 8/2008 | Brown et al. .................. 180/272 |
| 2003/0117287 A1 | 6/2003 | Crespo |
| 2005/0148828 A1 * | 7/2005 | Lindsay .................. 600/300 |
| 2005/0214169 A1 | 9/2005 | Leddy et al. |
| 2006/0130557 A1 | 6/2006 | Leddy et al. |
| 2006/0237253 A1 | 10/2006 | Mobley et al. |
| 2006/0238362 A1 | 10/2006 | Mobley et al. |
| 2006/0239856 A1 | 10/2006 | Mobley et al. |
| 2007/0144812 A1 * | 6/2007 | Stewart et al. .................. 180/272 |
| 2008/0154535 A1 * | 6/2008 | Sparks et al. .................. 702/130 |
| 2012/0025987 A1 * | 2/2012 | Mostov .................. 340/572.1 |

* cited by examiner

APPARATUS, SYSTEM, AND METHOD FOR IMPLEMENTING AND MONITORING BREATH ALCOHOL TESTING PROGRAMS, USUALLY FROM A FIXED POINT LOCATION, SUCH AS A HOME

CROSS-REFERENCE TO RELATED APPLICATIONS

This application is a continuation-in-part of U.S. Ser. No. 12/973,550, filed Dec. 20, 2010, which is a continuation of U.S. Ser. No. 12/504,714 filed Jul. 17, 2009, issued as U.S. Pat. No. 7,934,577 on May 3, 2011, which claims priority under 35 U.S.C. §120 to provisional application Ser. No. 61/081,594 filed Jul. 17, 2008, all of which are herein incorporated by reference in their entirety.

FIELD OF THE INVENTION

This invention relates to systems and methods for implementing and monitoring breath alcohol testing programs.

BACKGROUND OF THE INVENTION

Analyzing devices, used to determine the blood alcohol content of those about to drive vehicles, are commonly available. They emanated from breathalyzers used by law enforcement to test whether or not a driver was intoxicated, i.e., over the legal limit. In more recent times this traditional use of breathalyzing devices has been enhanced by combining a breathalyzer and an ignition locking system to prevent known, problem intoxicated drivers from being able to start their vehicle. This has been used with habitual violators in order to allow driving for necessary reasons, for example, to work, after confirming they are not intoxicated.

Typically at random times after the engine has been started the ignition interlock device will require another breath sample. The purpose of this is to prevent a friend (imposter) from breathing into the device to pass the test, thus enabling the intoxicated person to get behind the wheel and then drive away. If the breath sample isn't provided, or the sample given exceeds the ignitions interlock set blood alcohol level, the device will log the event, warn the driver, send a command station warning and begin visible and auditory warnings such as lights flashing, horn honking, etc.

Modern ignition interlock devices use an ethanol specific fuel cell for a sensor. A fuel cell is an electrochemical device in which alcohol undergoes a chemical oxidation reaction at a catalytic electrode surface (often platinum) to generate an electrical current. This current is then measured and converted to an alcohol equivalent rating. If it exceeds safe limits, warnings are issued.

A device log keeps a record of the activity on the device in the interlock vehicle electrical system. This record, or log, is printed out or downloaded each time the device sensors are calibrated, commonly at 30, 60 or 90 day intervals. Authorities may even require periodic review of the log. If violations are detected, then additional sanctions can be implemented. The typical periodic calibrations performed use either a pressurized alcohol/gas mixture at known standard alcohol concentration to test accuracy, or an alcohol wet bath (Guth) arrangement that contains a known standard alcohol solution. Cost of installation, maintenance and calibration are generally paid by the offender, which typically can run $100 a month or more.

A breath alcohol ignition interlock device is typically comprised of two components. One is a handheld component that contains the fuel cell to contain the electrochemical reaction and response after gathering the initial breath data. The second component is a relay box that relays the information and data from the first hand held unit to a command station or to provide a warning alarm, such as lights flashing, horn honking, etc or both. Both parts of the device offer opportunities for mischief, if one is inclined to try and beat the device and forestall court penalty sanctions, etc. Put another way, for the devious user on whom courts have already imposed enforced use of an ignition interlock device, often there is a "match of wits" between the ignition interlock device manufacturer and the user.

Some obvious attempts at avoiding the consequences of use of an ignition interlock device include imposter fraud, i.e., someone else other than the intoxicated driver provides the breath sample or no breath sample at all, but simply use of stored fresh air. A third and perhaps more daring and reckless attempt by one under the influence is deactivation, simply by attempts at disconnecting or even destruction. A fourth and perhaps a more subtle evidentiary way of avoiding the consequences of detection of excess use of alcohol is simply to deny the accuracy of the device, i.e., a fuel cell that has gone "haywire".

Manufacturers have done some things over the years to try and eliminate the risk of each of these avoidance techniques. For example, co-owned and commonly assigned application of some of these current inventors is U.S. Pat. No. 5,426,415 issued Jun. 20, 1995, is a breath temperature sensor to measure temperature of the breath sample to ensure that is the same temperature as normal human breath, thereby avoiding use of other non-human air sources. The '415 patent also requires rolling retests to ensure that the driver is the one that was tested and remains sober. U.S. Pat. No. 6,748,792 relates to use of video camera surveillance to capture the identity of the person being tested. U.S. Pat. No. 6,026,674 teaches use of detectors to detect use of alcohol removing filter media, such as activated charcoal by detecting the resultant low pressure caused by the pressure drop across an alcohol filter.

From the above it can be seen there are many "wily ways" of seeking to circumvent a breath alcohol ignition interlock device. A reliable interlock device avoids as many of these as possible, and detects the fraud, sending a signal to a command station, etc. That is, a good interlock device records attempts to physically tamper with it, detects circumvention or retest fraud attempts including disconnect efforts, and reports non-human air samples or attempts to filter out the breath, or mask the amount of alcohol blown into the device, and finally records and logs for evidentiary purposes each use.

One of the properties associated with high integrity breath alcohol ignition interlock devices is a need for proof of calibration. Calibration is expensive, and depending on the device, it needs to occur every 30, 60 or 90 days. Calibration usually involves the wet chemistry of known standards or a Guth bath. While necessary problems with calibration involve time consumption, expense of distant travel that may be necessary, inconvenience discourages expense and the travel to maintain integrity and the user's knowledge that lack of an adequately calibrated machine may make the evidence it collects inadmissible in court discourages the effort. One way all of this could be avoided is to develop a machine that self calibrates. That is to say, it internally reports information that could be used as States evidence that it is constantly calibrated. This would save money, time and expense of all concerned.

Yet another problem with alcohol ignition interlock devices is constant user circumvention by imposter fraud. As mentioned there are a variety of existing state-of-the-art techniques that have been used to detect such fraud and also to detect artificial samples. Some detectors that are used detect attempts to filter out alcohol from the breath; others take a video of the person blowing into the breathalyzer. With the latter, this can be avoided by one person blowing into the breathalyzer and then a different person driving. A circumvention frustration technique that is used by this invention is using two video cameras, one to detect the person blowing into the breathalyzer and a second to detect the person driving. If different people are recorded on these two different videos, the system senses and keeps a video record of this. As far as the present Applicants know, no one has so far used two video cameras, one focusing on the person taking the test and the other focusing on the driver, in order to be sure they are the same.

Another device useful for the present invention to detect circumvention efforts is the use of an accelerometer both in the handheld unit and in the relay box to immediately sense attempts at destruction and send a warning to a command station that such activity is occurring. If desired, this may even be coupled with a GPS to report location.

While most circumvention detection systems focus on the handheld unit, this invention also makes use of detection systems on the relay unit. Therefore it even further frustrates circumvention efforts. In particular, it also uses an internal cell phone which calls back to a command station when there is a sobriety violation and it may use a wireless link (RFID technology) between the handheld unit and the relay box in order to avoid circumvention efforts by wire cutting.

In addition to alcohol ignition interlock devices, there are other situations where it is necessary or desirable to test, record, and report a person's breath alcohol level. For example people under house arrest or on probation may have as a condition of remaining out of prison not consuming alcohol, or not getting intoxicated. This can require random or periodic breath tests, apart from the situation where the involved person intends to operate a motor vehicle. These "in-home" breath tests are subject to the same efforts to defeat or circumvent the system as the ignition interlock devices. In some cases it is necessary for the device to be portable such that the user can take it with them wherever they are, for example, home, to provide the necessary breath sample at the required time, from, for example, work.

Another disadvantage of many present interlock devices is the time delay in reporting any transgressions. Systems that merely record violations or potential violations in a log for later viewing suffer from a lack of immediacy. Users who are inclined to circumvent the system may feel that whatever punishment that will occur at a remote time when the violation is eventually reported is not sufficient deterrent to the immediate desire for a drink.

Accordingly, it is a primary object of the present invention to provide a self calibrating breath alcohol ignition interlock device.

Another important objective as seen from the above discussion is to provide a unit with enhanced ability to detect circumvention efforts such as imposter fraud, artificial air sample, deviation by destruction, etc. This unit may be in so-called home united or an ignition interlock.

The invention features of novelty which characterize it are pointed out with particularity in the claims which form a part of this disclosure. For a better understanding of the invention, its operating advantages and how its specific objects are achieved, reference is made to the accompanying drawings and the descriptive matter in which preferred embodiments of the invention are illustrated. It is to be understood that all of these features need not be used in the same unit, and that improvements in existing devices may be achieved by any one of the additional advantageous or improvements described herein for either the handheld unit or the relay box used alone or in combination.

BRIEF SUMMARY OF THE INVENTION

According to one embodiment of the present invention, an in-home or office or other fixed location breath alcohol monitoring apparatus includes a handheld breath alcohol testing device capable of receiving a breath sample and testing the breath sample to determine an alcohol content. An image recorder adapted to record image data when the breath sample is provided. A sealed case encloses an electronic storage medium that is in communication to receive information about the determined alcohol content. The storage medium is also adapted to receive image data associated with the breath test. A communication device is mounted within the sealed case for transmitting data related to the determined alcohol content and the associated image data to a remote service provider. The electronic storage medium and the communication device may be contained within a relay box mounted inside the sealed case. The relay box may include a compass and/or an accelerometer for determining attempts to tamper with the sealed case or the handheld testing device. A speaker may be mounted within the sealed case. The sealed case may include a cover and a mechanism for detecting attempts to remove the cover. A GPS receiver may be provided in communication with the electronic storage medium to provide GPS data to the electronic storage medium associated with each breath sample. An antenna unit including the GPS receiver and an antenna for the communication device may be provided external to the sealed case. A mount may be provided on an exterior of the sealed case for supporting the image recorder. The sealed case may have connection sockets for electronically connecting the electronic storage medium with: the image recorder, the handheld testing device, and a GPS receiver. The electronic storage medium may record instances when any of the image recorder, the handheld testing device, or the GPS receiver have been disconnected from the electronic storage medium. Basically this so-called "in-home unit" has the same features as the ignition interlock except the ignition interlock has been eliminated.

According to the embodiment of the present invention directed to a system for administering an in-home breath alcohol testing program, the system includes a handheld breath alcohol testing device capable of receiving a breath sample and testing the breath sample to determine an alcohol content, a sealed case enclosing an electronic storage medium in communication with the handheld testing device to receive an indication of the determined alcohol content, a communication device mounted within the sealed case for transmitting data related to the breath alcohol testing, and a service provider computer system adapted to receive the data related to the breath alcohol testing. The service provider computer system may be adapted to generate a viewable log with information regarding the data related to the determined alcohol content, wherein the viewable log is stored on the service provider computer system such that it can be viewed via the Internet by a monitoring authority provided with access to the viewable log. The service provider computer system may be adapted to recognize when the received data related to the breath alcohol testing indicate that a protocol established by the monitoring authority has been violated and to provide a visual indication within the viewable log of any such violation. The service provider computer system may adapt to generate a message that gets sent to the monitoring authority regarding any such violation. The service provider computer system may be adapted to recognize when the received data related to the breath alcohol testing indicate that any of a plurality of protocols established by the monitoring authority has been violated and to provide a visual indication within the viewable log of any such violation. The service provider computer may be adapted to generate a message that gets sent to the monitoring authority when specified ones of the plurality of protocols are violated. The viewable log may include geographic information regarding the location where the breath sample was received. The service provider computer system may be adapted to send a message to the monitoring authority if the GPS coordinates indicate a geographic location that is not acceptable. The data related to the breath alcohol testing may include image data recorded when the breath sample was received, and the viewable log may include an image created from the image data.

According to another embodiment, the present invention is directed to a method of administering a breath alcohol testing program that includes the steps of receiving information at a service provider computer system from a breath alcohol testing unit, automatically generating a viewable log based on the received information, and permitting a monitoring authority to access the log via the Internet. The method may also include providing a visual indication within the viewable log when the received information indicates that a protocol established by the monitoring authority has been violated. The method may also include automatically sending a message to the monitoring authority when the received information indicates that a protocol established by the monitoring authority has been violated. The breath alcohol testing unit may be an in-home unit or may be an ignition interlock device. The information related to the breath alcohol testing may include geographic information indicating a location where the breath sample was received, and a determination may be made as to whether the location where the breath sample was received is within a permitted area. The information related to the breath alcohol testing may include image data recorded when the breath sample was received, and a determination may be made as to whether the image data is consistent with the geographic information.

In some embodiments, the invention relates to an improvement in a breath alcohol test device that includes within the handheld unit a fuel cell and a miniaturized self calibrating test device for the fuel cell thereby avoiding the need for 30, 60 and 90 day calibration testing. It also relates to various tamper proof or circumvention improvements that may be used alone or in combination with the self calibration improvement.

According to one embodiment the present invention is directed to a vehicle breathalyzer device that includes a breath alcohol testing device adapted to collect a breath sample from a possible driver of a vehicle. The device also includes a first image recorder that records an image of the possible driver of the vehicle each time the driver provides a breath sample to the breath alcohol testing device and a second image recorder that records a verification image each time the breath sample is provided. The verification image may permit a determination of whether the possible driver is in a driver's seat of the vehicle when the breath sample is provided. The first and second image recorders may both be provided in the breath alcohol testing device, or the second image recorder may be mounted within the vehicle apart from the breath alcohol testing device in a location such as on the windshield. If the first and second image recorders are both provided as part of a handheld breath alcohol testing device the second image recorder may be aligned for pointing at the steering wheel as the breath sample is taken by a possible driver in the driver's seat. Additionally, the alcohol breath testing device may be associated with a separate relay box that is connected to the vehicle's electrical circuitry to impede operation of the vehicle if an acceptable breath sample is not provided.

According to another embodiment of the present invention a breath alcohol test device that has a breath tube, a fuel cell chamber in selective communication with the breath tube, and a pump for moving breath is improved by including a miniaturized Guth bath that periodically tests a headspace above a known-concentration alcohol sample to test the accuracy of allow self-calibration of the alcohol test device. The known-concentration alcohol sample may be provided within a sponge. The fuel cell chamber may include an outlet in communication with the pump and an inlet in communication with a control valve that can be adjusted to connect the inlet with the breath tube to test a breath sample and to connect the inlet with the headspace to perform a calibration test.

According to another embodiment, the present invention is a vehicle interlock breathalyzer system that includes a handheld part that has a breath sample collection and testing unit, and a relay box in connection with an electrical system of a vehicle to impede operation of the vehicle if an acceptable breath sample is not provided to the breath sample collection and testing unit. A first accelerometer is associated with either the handheld device part or the relay box part to detect attempts at destruction. The relay box part may include a computer memory for recording any detected attempts at destruction. A cell phone may be provided in the relay box part to report any recorded attempts at destruction. A second accelerometer may be provided in the relay box part or hand held part so that both parts include an accelerometer for detecting attempts at destruction. The first accelerometer may detect vehicle motion and record detected motion without an associated acceptable breath test as a possible violation event.

According to another embodiment of the invention, a vehicle interlock breathalyzer system that includes a handheld part with a breath sample collection and testing unit and a relay box part in connection with an electrical system of a vehicle to impede operation of the vehicle if an acceptable breath sample is not provided to the breath sample collection and testing unit, is improved by including: an electrical circuit within the relay box that detects the polarity of an ignition circuit of the vehicle, and a computer processor within the relay box that adjusts the relay box operation in accordance with the detected polarity.

DETAILED DESCRIPTION OF THE PREFERRED EMBODIMENT

Figure 1:
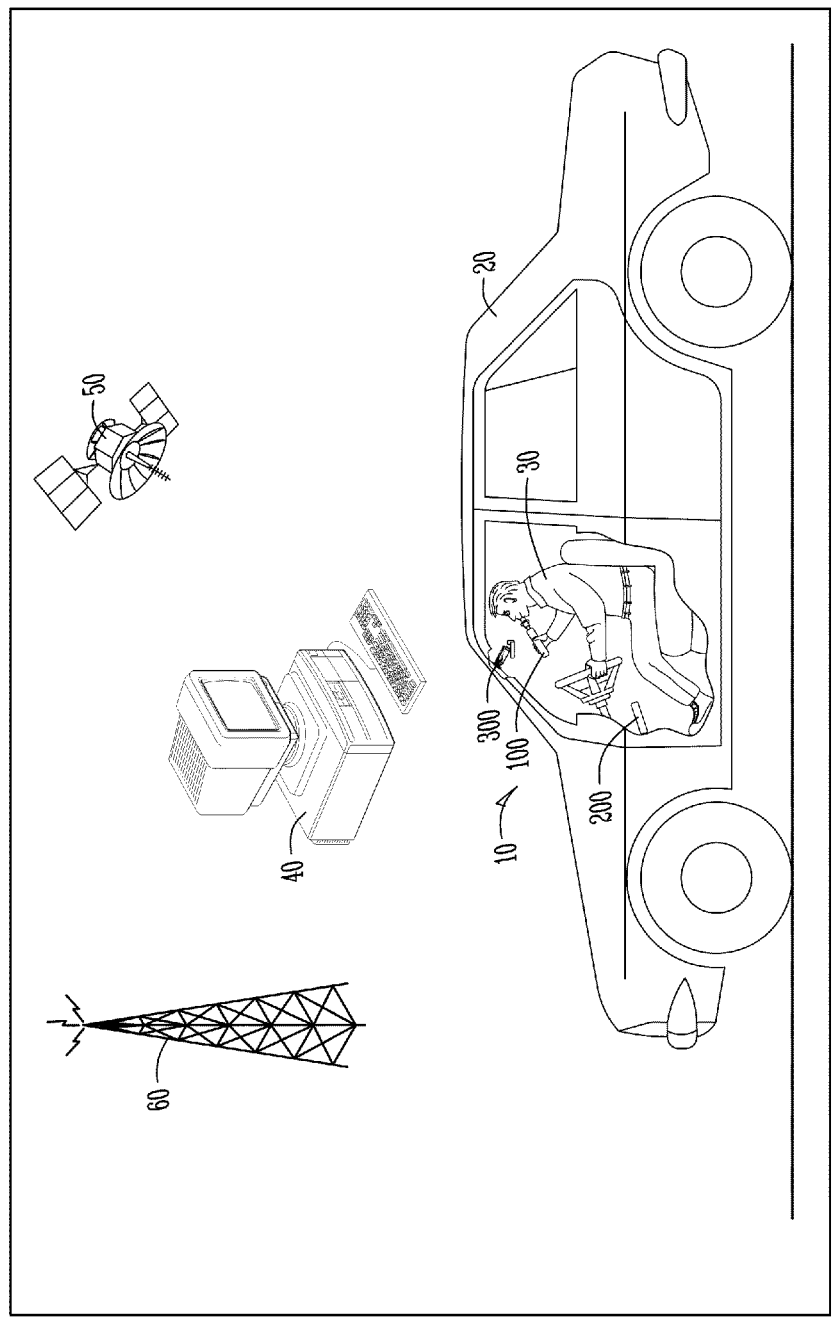
FIG. 1 is a schematic showing the components of a breathalyzer ignition interlock system according to one embodiment of the present invention.

FIG. 1 shows a breathalyzer ignition interlock device 10 according to one embodiment of the present invention. The interlock device 10 includes two primary components, a handheld unit 100 and a relay unit 200. The embodiment shown in FIG. 1 also includes a separate camera unit 300 that may be omitted in some embodiments. The handheld unit 100 contains the alcohol sensor and the user interface portions of the device 10. The relay box 200 provides a vehicle systems interface and is equipped to communicate with an outside service provider. The ignition interlock device 10, which may also be referred to herein as an interlock system, provides a mechanism for measuring breath alcohol content, for disabling a vehicle based on the measured alcohol content, for preventing or detecting attempts to cheat or tamper with the system, and for logging and reporting tested data and imaging.

The general arrangement of the interlock system 10 in use is illustrated in FIG. 1. A driver 30 that wishes to operate a motor vehicle 20 must first provide a breath sample to the interlock system 10 through the handheld unit 100. The handheld unit 100 analyzes the breath sample, and communicates the results of the test to the relay 200. If the results of the test are acceptable, the relay 200 will permit the driver 30 to engage the ignition and start the engine of the vehicle 20. If, however, the results of the test indicate that the blood alcohol content is above an acceptable level, the relay 200 will lock out the ignition of the automobile 20 to prevent operation of the vehicle 20 by an intoxicated driver. As discussed in greater detail below, the relay 200 may be provided with a cellular phone and GPS device that communicate via satellite 50 and/or cell phone tower 60 with a remote computer 40 that may be controlled by a service provider. The service provider may be a third party commercial organization that facilitates the monitoring and maintenance of the system 10. Alternatively, the service provider could be a governmental agency or a private company that has a fleet of vehicles and drivers. Greater detail regarding each of the components and operation of the breathalyzer ignition interlock device 10 according to the present invention are provided below.

Handheld Device

Figure 2:
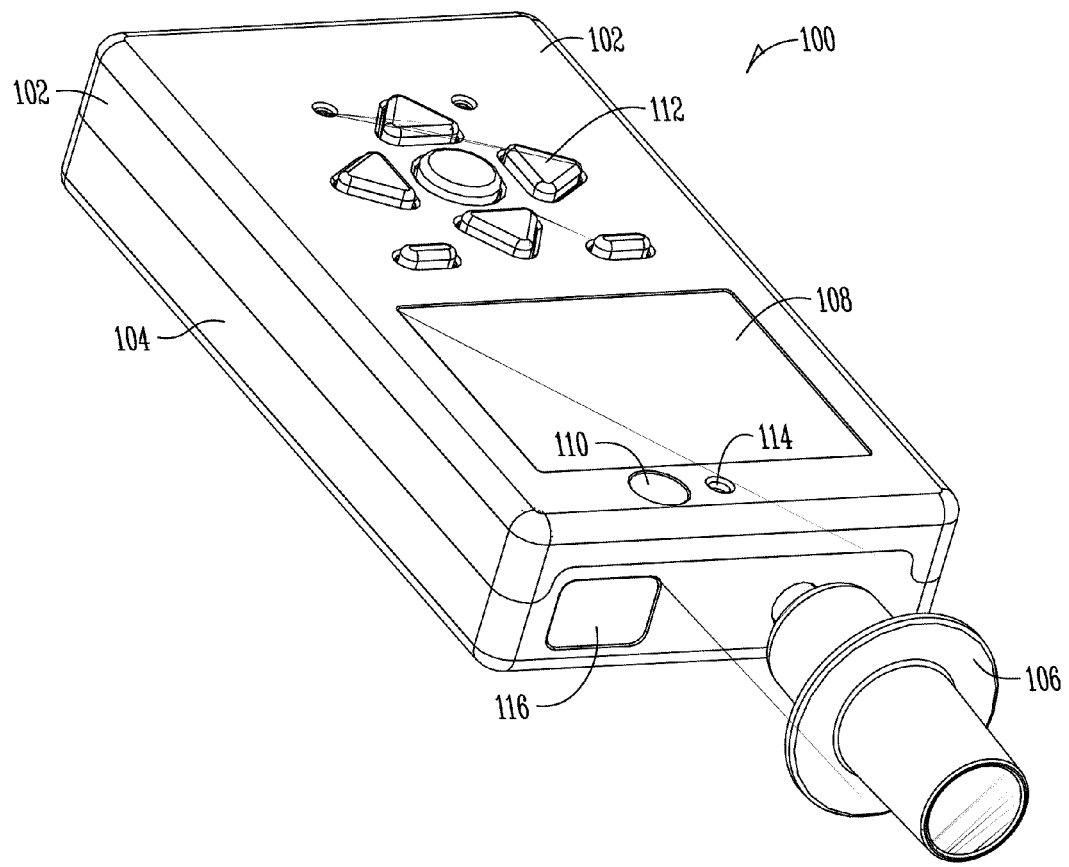
FIG. 2 is a perspective view of a top front side of a handheld device according on one embodiment of the present invention.

FIG. 2 is an isometric view of a handheld unit 100 according to one embodiment of the present invention. The handheld unit 100 includes an outer case formed by a top shell 102 and a bottom shell 104. The outer case is preferably a relatively hard durable material that serves to protect the internal components of the handheld unit 100. The shells 102 and 104 may be formed by injection molding of hard plastic, or other similar material. Preferably, they are joined together in a fashion that permits access to the internal components of the device 100 without destruction of the outer case. For example, threaded fasteners may be used to join the top shell 102 to the bottom shell 104 (see FIG. 3).

A blow tube 106 is provided at one end of the case. In the embodiment shown, the blow tube 106 extends into an opening formed in the bottom shell 104. Preferably the blow tube 106 will be removably insertable into the handheld unit 100 by friction fit, or similar mechanism. This permits each driver to have their own blow tube 106 for sanitary reasons, and it also permits easy cleaning or replacement of the blow tube 106. An internal passage of the blow tube 106 will preferably include obstructions (not shown) to deflect and retain saliva or other contaminants that might be expelled while providing a breath sample. In this fashion, the external blow tube 106 acts as a spit trap.

The handheld unit 100 also includes a display screen 108 to provide a visual interface for a user. In a preferred embodiment, the display screen 108 is a color liquid crystal display with back lighting. An ambient light sensor 110 may be provided to automatically adjust the brightness of the display screen 108. Alternatively, a user may be able to adjust the brightness of the display screen 108 as desired. The display screen 108 may be used to show operating instructions, device status, and communications from a service provider.

The handheld unit 100 is provided with a keypad 112 to allow a user to operate and control the handheld unit 10. In the preferred embodiment shown, the keypad includes arrow keys and other function keys that may be dedicated to a specific purpose, or may have "soft" functionality as dictated by the current operating needs of the system. In alternative embodiments, the keypad 112 may be a small alpha numeric keyboard of the type found on cell phones or may even be a small "qwerty" keyboard as might be found on text messaging machines.

The handheld unit 100 may also be provided with a microphone 114 in order to receive audio input from a user. The audio input may be stored in the form of digital sound files, or may be used to communicate through a cell phone that may be provided in the handheld unit 100, or more preferably in the relay box 200. The handheld unit 100 may communicate with the relay box 200 by Bluetooth, radio frequency, or by a wire connection between the handheld unit 100 and the relay box 200.

A camera cover 116 is provided in the bottom shell 104 to protect the camera (not shown in FIG. 2, see FIG. 5) that is used to capture the image of a driver 30 as the driver 30 provides a breath sample into the blow tube 106. The camera cover 116 should be transparent to permit the camera to capture an accurate image of the driver 30.

Figure 3:
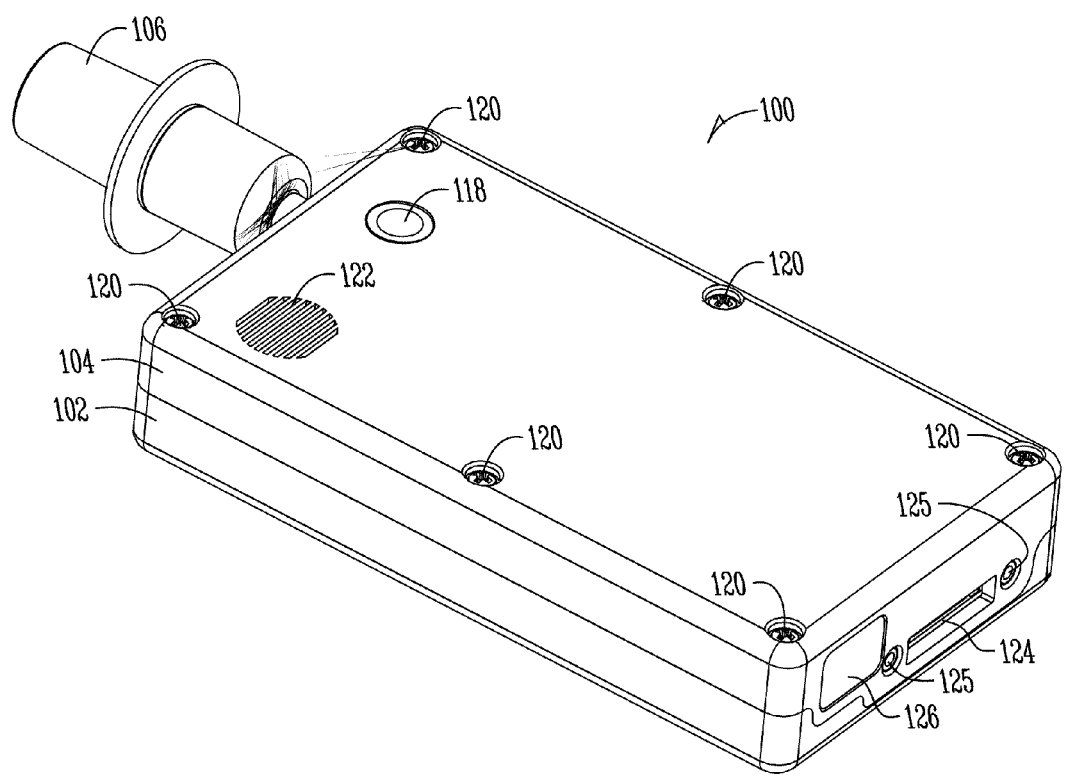
FIG. 3 is a perspective view of a bottom rear side of the handheld device of FIG. 2.

FIG. 3 shows the handheld unit 100 of FIG. 2 flipped over to reveal the bottom side of the handheld unit 100. The top shell 102 is fixed to the bottom shell 104 by small bolts 120. Those skilled in the art will be aware of other suitable mechanisms for releasably connecting the top and bottom shells 102 and 104 together. The shells 102 and 104 are provided with a mechanism for sensing when the case of the handheld unit 100 has been opened. For example, the bottom shell 104 may be provided with a permanent magnet that is located in close proximity to a Hall effect sensor provided in the electronics for the handheld unit 100. If the bottom shell 104 is removed in order to provide access to the electronics, the Hall effect sensor will detect the movement of the permanent magnet away from the sensor, and the handheld unit 100 will record the event, which may indicate that the unit 100 has been tampered with.

An exhaust tube 118 provides an outlet for breath samples that have been provided through the blow tube 106. As discussed in more detail below in reference to FIG. 5, the exhaust tube 118 has provided within it a sensor for sensing the temperature of the breath sample to assure that it is at or near body temperature. The exhaust tube 118 has provided within it a small sample tube (these not shown in FIG. 3) from which the actual breath sample to be tested is withdrawn. The handheld unit 100 is also provided with sensors to sense whether air is being sucked through the exhaust tube, rather than blown into the blow tube 106 in an attempt to defeat the system.

Figure 4:
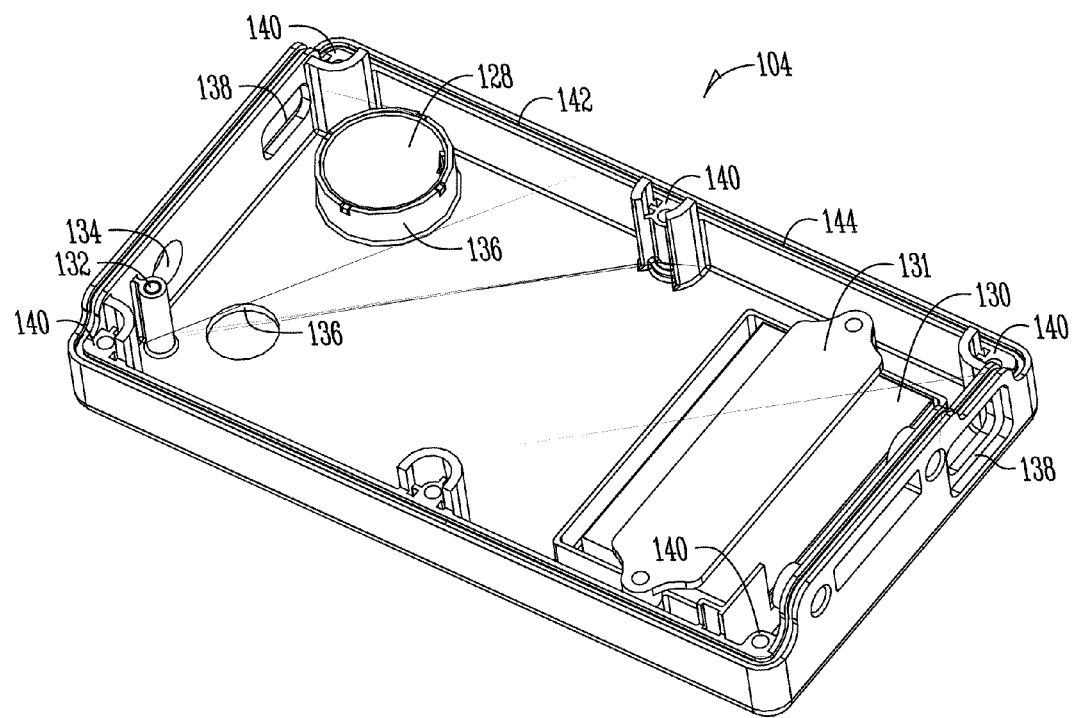
FIG. 4 is a perspective view of the bottom shell of the handheld device of FIG. 2.

Openings 122 are provided in the bottom shell 104 for alignment with a speaker (see FIG. 4).

An input jack 124 is provided at one end of the handheld unit 100. The input jack 124 may be an RS 232 serial port or a USB host port. The input jack 124 can be used to transfer data back and forth with the relay box 200, and may be used to provide power to the handheld unit 100 or to provide power to charge a battery provided within the handheld unit 100. Threaded receivers 125 are provided adjacent to the input jack 124 for fixing an input plug to the input jack 124.

A camera cover 126 is provided in the handheld unit 100 in an opposite end from the blow tube 106. The camera cover 126 protects a camera (not shown in FIG. 3, see FIG. 5) that may be used to capture an image of the surroundings when a breath sample is corrected, in order to verify the location of the handheld unit 100 within the car 20 at the time the sample is provided.

FIG. 4 shows the interior of the bottom shell 104. Speaker 128 is mounted within a speaker holder 129 integrally formed with the bottom shell 104. A battery 130 that is used to provide power to the various components of the handheld unit 100 is provided within a battery holder 131. Preferably the battery 130 is a lithium ion rechargeable battery. A permanent magnet 132 is mounted within a sleeve 133. The permanent magnet 132 aligns with a Hall effect sensor (see FIG. 5) to form a mechanism for detecting when the case or the handheld unit 100 has been opened. The bottom shell 104 includes an opening 134 for receiving the blow tube 106. An opening 136 is provided through the bottom plate of the bottom shell 104 to provide an opening for the exhaust tube 118. Each end of the bottom shell 104 is provided with an opening 138 for the digital cameras. Six receivers 140 are provided around the periphery of the bottom shell 104 for receiving small bolts 120 that connect the top shell 102 to the bottom shell 104. A trench 142 is provided around the perimeter of the bottom shell 104 for receiving a tongue that protrudes from the top shell 102 and matingly engages the trench 142 in order to maintain the shells 102 and 104 in place, and to provide a water tight seal between the two shells 102 and 104.

Figure 5:
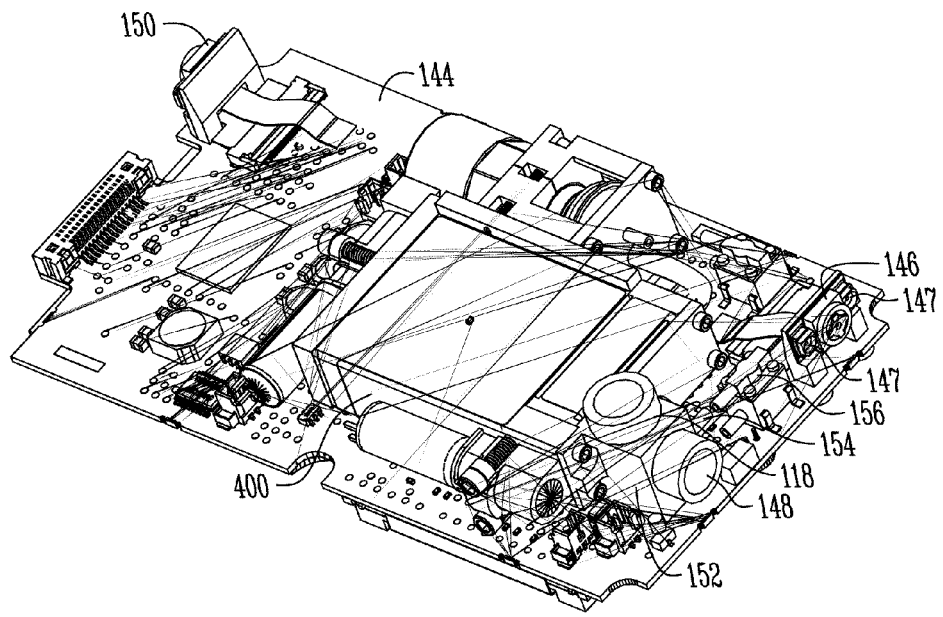
FIG. 5 is a partial perspective view of the internal components of the handheld device of FIG. 2.

The internal components of the handheld unit 100 are shown in FIG. 5. The components are mounted on a printed circuit board (PCB) 144. A first camera 146 is mounted on the same end of the PCB 144 at the breath tube inlet 148. A second camera 150 is mounted at the opposite end of the PCB 144 from the first camera 146. The second camera 150 is used for capturing images as a breath sample is taken to verify the location of a handheld unit 100 within the vehicle 20. Preferably, the cameras 146 and 150, which may also be referred to as imagers, image recorders, or image capturing devices, have the capability to operate in dark environments using infrared (IR) illumination. To accomplish this, the cameras 146 and 150 are provided with IR light emitting diodes 147. The cameras 146 and 150 include custom lenses that allow the passage of IR wavelengths. This permits the cameras 146 and 150 to be operated safely in the vehicle 20 after dark, when a driver 30 has dark adapted vision, and could be temporarily blinded by a bright light within the vehicle 20. The use of IR illumination allows the system to have nearly the same image capturing capabilities regardless of ambient light. Generally speaking, images taken in daylight will record as color images, and those taken under IR illumination will record as monochrome images. The cameras 146 and 150 may be capable of capturing video images or still images, or both. The cameras 146 and 150 are connected to a central processing unit (CPU) (not shown) provided on the PCB 144. The CPU includes both RAM and FLASH memory needed for operation and long term storage of data.

The breath tube inlet 148 and the exhaust tube 118 are provided as part of a breath directing block 152. The breath directing block includes a side tube 154 that leads to a transducer 156 positioned immediately above stream from a constriction in the airway, such that the transducer 156 can be used to verify that the sample is being provided by blowing through the blow tube 106 and not by sucking air through the exhaust tube 118.

Also connected with the CPU is a codec (not shown). The codec converts digital audio information to an analog signal and vice versa. In addition to being connected to the CPU, the codec is connected with a microphone 114 (see FIG. 2) and the speaker 128 (see FIG. 4). Audio outputs from the CPU are converted from a digital signal into an analog signal and then amplified and sent to the speaker. This allows the unit 100 to provide spoken messages and sounds to the user 30. Similarly, the microphone converts sound into an electrical signal that is received by the codec and digitized into a form that can be read and stored by the CPU. The CPU can transmit the digital audio files to the relay box 200 by Bluetooth, radio frequency, or hardwire connection. The relay box 200 can log and save the audio files, or may transmit them on to a service provider 40 (see FIG. 1) via a cellular phone provided in the relay box 200.

Each handheld unit 100 contains an integrated circuit programmed by its manufacturer with a unique serial number. This serial number can be embedded in any communications from the handheld unit 100 to uniquely identify the unit.

Breath Test Assembly

Figure 6:
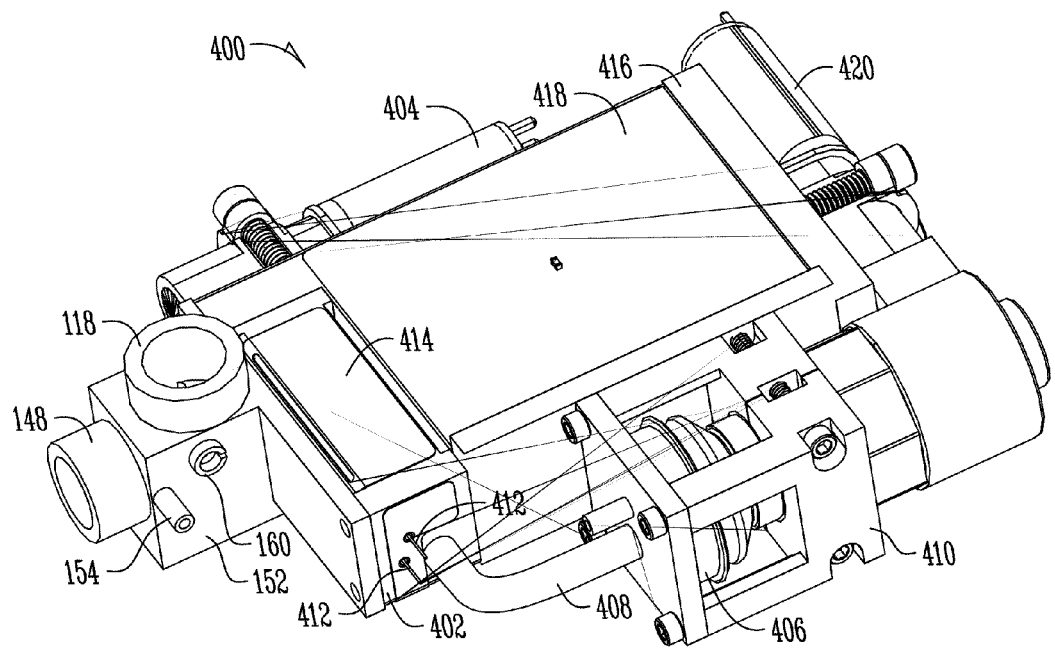
FIG. 6 is a perspective view of the components of the breath testing assembly from the handheld device of FIG. 2.
Figure 7:
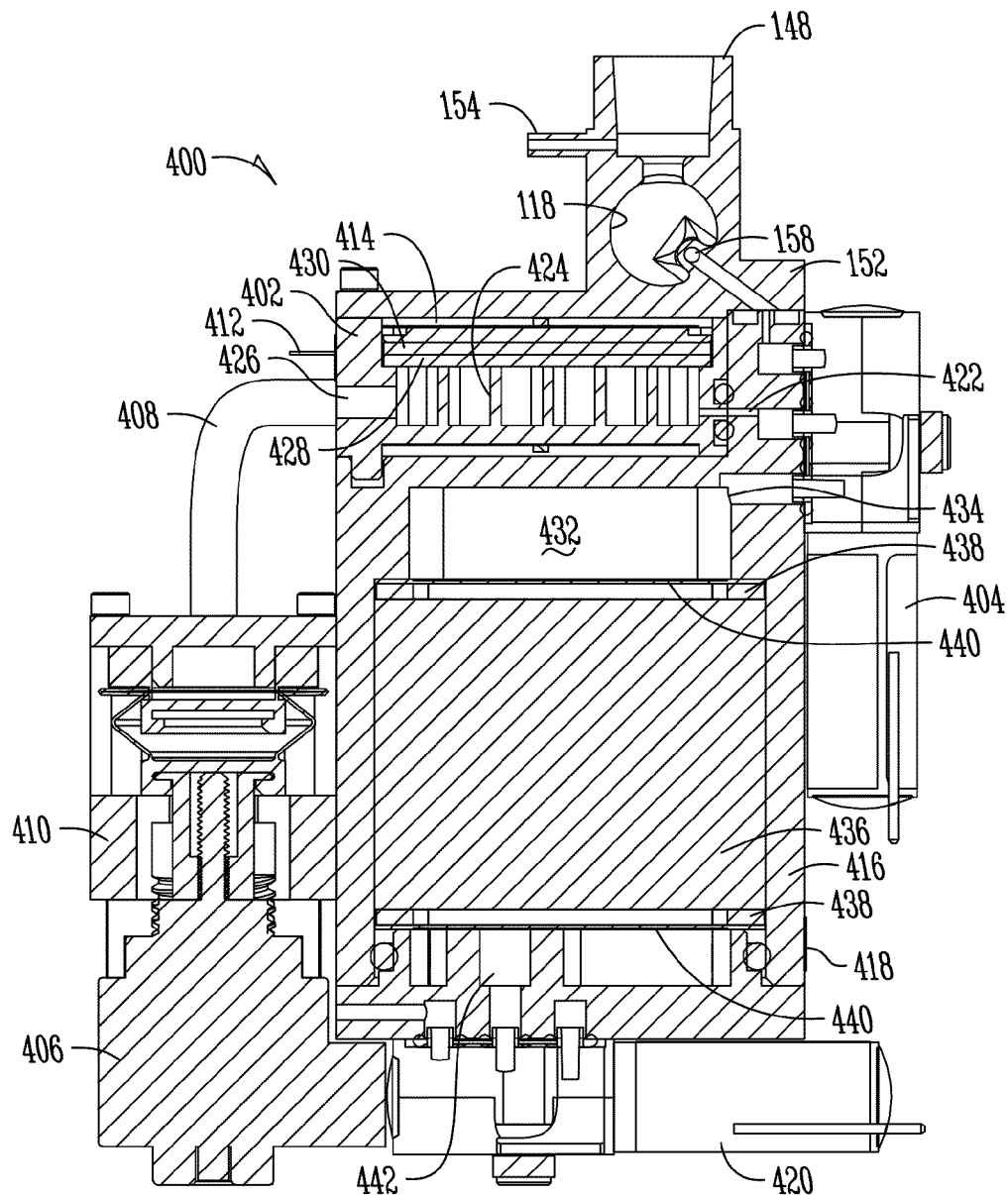
FIG. 7 is a partial cross-section view of the breath testing assembly of FIG. 6.

A breath alcohol tester assembly 400 is provided on the PCB 144, and is shown in more detail in FIGS. 6 and 7. The breath alcohol tester assembly 400 contains all of the components needed to detect a breath sample airflow, measure temperature and pressures to prevent cheating on the test, convert any alcohol content to a measurable electrical signal, and to calibrate itself. With reference to FIGS. 6 and 7, it can be seen that the exhaust tube 118 includes a sample inlet 158. The sample inlet 158 is used to withdraw a portion of the breath sample to be tested for alcohol content. The breath directing block 152 is mounted to a fuel cell 402. The sample inlet 158 provides a passage into the fuel cell 402 via a valve 404. The fuel cell 402 is adapted to catalytically combine any alcohol in a sample introduced into the fuel cell 402 through the inlet 158 with oxygen to create an electrical signal that is amplified and measured to determine an alcohol concentration in the breath sample in a known fashion. A pump 406 is connected to the fuel cell 402 by tube 408. The pump 406 is used to supply a vacuum to the fuel cell 402 at the opposite end of the sample inlet 158. The pump 406 is used to extract the desired sample volume at the desired portion of the breath sample. The pump 406 is mounted within a pump bracket 410. Outlet wires 412 connect with electrodes inside the fuel cell 402 and provide the voltage output for amplification and analysis. A flex heater 414 surrounds the fuel cell 402 in order to heat the fuel cell 402 to a proper operating temperature. A flex heater 414 may also include a temperature sensing mechanism. Preferably the temperature of the fuel cell 402 is maintained at 34° C. to keep it above the sample temperature and to prevent condensation of water or vapors. The accuracy of the conversion process is also aided by maintaining a known temperature because the fuel cell catalytic process is temperature dependent. Also connected to the fuel cell 402 through the valve 404 is a calibrator housing 416. The calibration housing 416 includes internally a water alcohol mixture with a known alcohol concentration that can be used to calibrate the system. The valve 404 is a three-way three position solenoid valve. In a first position, it connects the sample inlet 158 with the insides of the fuel cell 402. In a second position, the valve 404 connects the interior space of the calibration housing 416 with the internal compartments of the fuel cell 402. In a third position, the valve 404 closes all of the inlets. A flexible heater 418 surrounds the calibration housing 416 to provide heat to the calibration housing 416 and maintain it at a desired temperature such that the alcohol vapor concentration within the calibration housing 416 is maintained at a proper level. A temperature sensor is also provided as part of the heater 418, or as a separate element in order to sense the temperature. Preferably, the calibration housing 416 will be made from aluminum, or other similar material that readily conducts heat. Second valve 420 is provided in association with the calibration housing 416 to control the flow of air at the upstream side of the calibration housing 416.

The details of the breath alcohol tester assembly 400 can be seen in FIG. 7, which shows a cross section of the assembly 400 from FIG. 6. When a breath sample is provided, the flow of air through the assembly 400 begins at the breath tube inlet 148. The majority of the breath sample passes through the inlet tube 148 and out the exhaust tube 118. The approximate quantity of breath provided is monitored by sight tube 154 that extends into the breath inlet tube 148 and is used to measure the pressure and duration of the blow. The temperature of the sample is also monitored with a thermocouple (not shown) within the exhaust tube 118. After a sufficient volume of breath has been provided through the inlet tube 148, a small test sample of the breath is withdrawn through inlet 158 which leads from the exhaust tube 118 to the valve 404. The valve 404 is adjusted into a test position that pneumatically connects the inlet passageway 158 with the inside of the fuel cell 402 through a fuel cell inlet 422. From there the test sample winds back and forth through weir 424 to the fuel cell outlet 426 that leads to the tube 408.

The pump 406 is preferably a small bellows-type pump. The pump 406 is used to selectively withdraw a test sample through the fuel cell 402. The pump 406 is preferably able to selectively provide either a vacuum or a positive pressure through the tube 408. To withdraw a test sample through the fuel cell 402 as described above, a vacuum is applied through the tube 408. In order to assure no migration of the initial portion of a blow into the fuel cell 402, it is preferred to provide a slight positive pressure through the tube 408 prior to opening the valve 404 to permit the withdrawal of a test sample.

As the test sample flows through the fuel cell 402, the test sample comes in contact with electrode 428. The oxidation of any alcohol within the breath sample creates a current which is transformed to a difference between electrode 428 which is in contact with the sample and electrode 430. Outlet wires 412 that are connected to the electrodes 428 and 430 are used to convey the voltage difference to a computer which is able to convert the voltage to an estimated alcohol content within the breath sample, and hence an estimated of the test subject's test blood alcohol content.

The breath alcohol tester assembly 400 can be set to withdraw a calibration test sample from the calibration housing 416. To test a calibration sample, the valve 404 is adjusted to connect a head space 432 within the calibration housing 416 to the fuel cell inlet 422 through calibration housing outlet 434. Within the calibration housing 416 is a sponge 436 is provided that is saturated with a solution of water and alcohol that has a known concentration of alcohol. The sponge 436 is held in place within the calibration housing 416 between gaskets 438 that space the sponge 436 apart from breathable covers 440. The breathable covers 440 should be air permeable, water tight. A material sold under the brand name Gore-Tex which has openings or passageways small enough to prevent water from passing across the fabric, but large enough to permit air to pass through the fabric may be used to form the breathable covers 440.

If the calibration housing 416 and therefore the solution within the sponge 436 is maintained at a known temperature, the concentration of alcohol vapor within the air in head space 432 should be a known concentration that correlates with the concentration of alcohol within the solution. To withdraw a calibration sample, the pump 406 provides a vacuum through the tube 408, and the valve 404 is adjusted to connect the calibration housing outlet 434 with the fuel cell inlet 422. A calibration sample then flows from the head space 432 through the outlook 434, then through valve 404 and into the fuel cell 402 through the fuel cell opening 422. Once inside the fuel cell 402, the calibration test sample flows back and forth through weirs 424 to come into contact with electrode 428 to cause oxidation and known voltage difference that can be measured. If the measured voltage corresponds with the known alcohol content of the sample solution within the sponge 436, then the blood alcohol tester assembly 400 is considered to be in proper calibration. If the measured voltage does not correspond with the known alcohol content of the sample solution, then the unit is not in calibration, and it may be necessary to obtain a new handheld unit 100, or to have the breath alcohol tester assembly 400 replaced. Valve 420 is used to control the flow of air into the calibration housing 416 through calibration housing inlet 442. The valve 420 is normally in a position to close inlet 442, but when a calibration sample is being withdrawn, the valve 420 is adjusted to permit the flow of air into the calibration housing 416 through inlet 442 in order to equalize the pressure within the housing 416.

Relay Box

Figure 8:
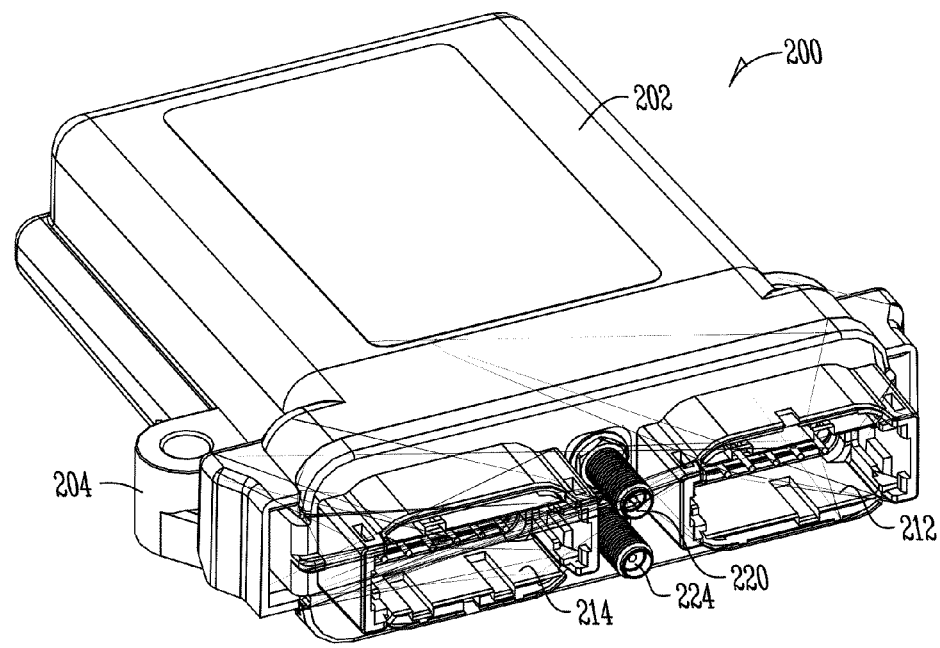
FIG. 8 is a perspective view of a relay box according to one embodiment of the present invention.
Figure 9:
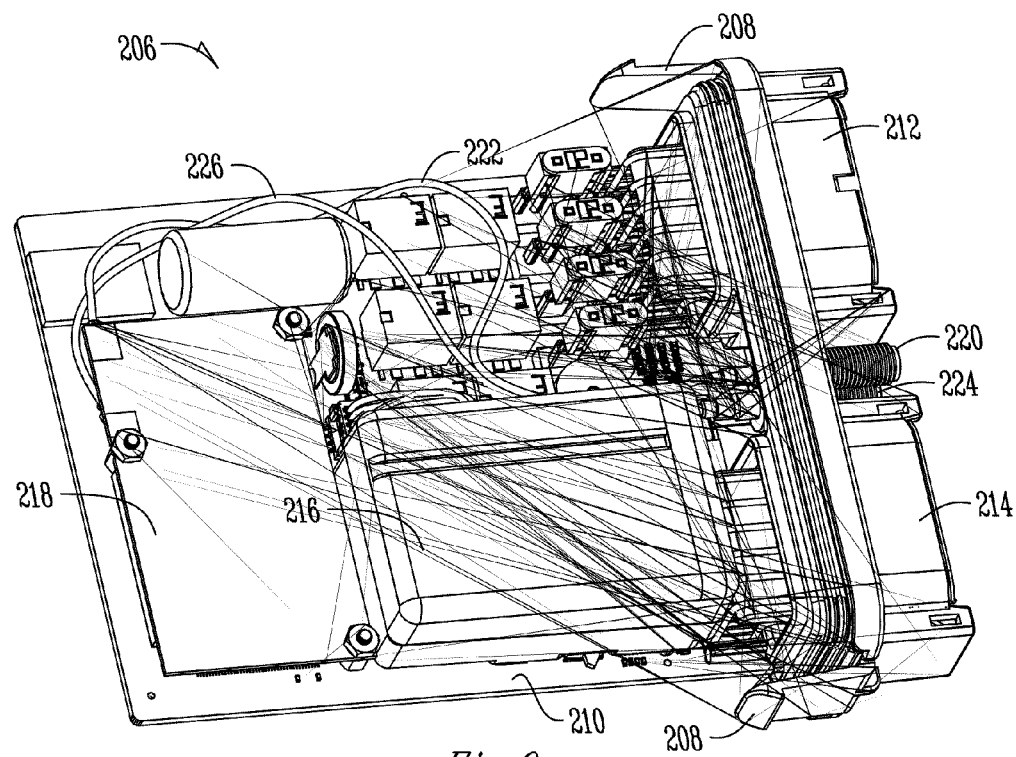
FIG. 9 is a perspective view of the internal components of the relay box of FIG. 8.

FIGS. 8 and 9 show the relay box 200 and its internal components. The relay box 200 is electrically connected with the electrical system of the vehicle 20 and can lock out the vehicle's ignition system unless and until an acceptable breath test sample has been given by a driver. The relay box 200 may also be connected to provide control of the vehicle's horn and lights. The relay box 200 includes an embedded computer system (not shown) to manage the functioning of the ignition interlock system as well as communications between the handheld unit 100 and the service provider (see FIG. 1). The computer system implements a file storage system in a non-volatile/memory to log test results, tampering events, calibration information, and other pertinent system information. The relay box 200 has a power system with three potential sources of power and the means for switching between them as the circumstances dictate. The primary power source for the relay box 200 is the vehicle battery (not shown). Circuitry is provided to condition the vehicle power and prevent damage to the relay box 200 from unwanted transient events on the vehicle power system. The relay box circuits are designed to minimize the draw on the vehicle battery by actively managing the activity of the relay box 200. The other voltages required by the relay box are all generated from the primary power by power supply circuits. The computer system is able to measure the voltage provided by the vehicle battery to ensure that it is sufficient to operate the relay box 200.

As seen in FIG. 8, the relay box 200 includes a rugged outer case 202 that includes mounting tabs 204 that permit the relay box 200 to be fastened to the interior of a vehicle. A relay box insert 206 that includes all of the internal components of the relay box 200 is shown in FIG. 9. The relay box insert 206 slides into and is retained within the outer case 202. The insert 206 is held within the outer case 202 by resilient ears 208. Any attempt to open the relay box 200 by removing the insert 206 from the outer case 202 will activate a switch (not shown). Any activity on the switch is saved by a circuit and it signals to the relay box computer system as a tamper event. The tamper event is logged and communicated to the service provider.

The components for the relay box 200 are provided on a printed circuit board 210. The insert 206 is provided with a vehicle interface connector 212 that is used to connect the relay box 200 with the various electrical systems of the vehicle. The insert 206 is also provided with a handheld unit interface connector 214 for hard wire connection to the handheld unit 100. A battery insulator 216 provides thermal insulation for a lithium ion battery that provides power to continue operation of the relay box 200 for a short period of time in the event that a vehicle power is removed from the relay box 200. A heater may also be provided within the insulation to assure that the battery is operational at extreme cold temperatures. The lithium ion battery is maintained in a full state of charge using the vehicle power. A disconnection from the vehicle power system would be recorded as a tamper event and reported to the service provider. Circuitry is provided to monitory the actual battery temperature and regulate the heater to maintain the battery at a desired temperature. A large value capacitor (not shown) is also provided on the PCB 210. The capacitor provides a final energy storage backup that is utilized only after the unit has been disconnected from the vehicle power supply, and the lithium ion battery has been exhausted. The capacitor will provide the system with enough operating time to allow the computer to log the event, a critical data to the flash memory, and to shut down in an orderly manner.

A cellular phone and GPS unit are provided on the insert 206 beneath a mounting plate 218. The GPS unit is attached to a GPS antenna jack 220 by wire 222. The cellular phone is attached to cellular phone antenna jack 224 by wire 226. The cellular phone is used to communicate data to the service provider. The GPS unit is used to track the geographic location of the relay box 200 and hence the vehicle to which it is attached. This can serve as a backup means of determining vehicle motion, as well as providing the location of the vehicle at the time of any tamper event. This function can also verify legitimate events such as the vehicle being serviced, if the location is that of a dealer or garage. Physically, the GPS receiver is built into the cellular phone module. The cellular phone, in addition to communicating logs of the test results to the service provider can update software installed on the relay box computer. The cellular phone may permit messages to be relayed to the operator, via the handheld unit, from the service provider. The cellular phone could even be used to notify authorities in the event of a failed breath test while the vehicle is in operation.

The Bluetooth short range wireless data link provides two-way communication between the relay box and the handheld unit. Both digital audio and video can be transmitted. Data from breath tests will be transmitted to the relay box for storage, along with images captured by the handheld unit cameras as part of the breath test. Relay box and vehicle status information can be transmitted from the relay box to the handheld unit for display. Communications from the service provider received by the cellular phone can be relayed by the handheld via the Bluetooth data link, or through the handheld unit interface connector 214. Each relay box 200 contains an integrated circuit programmed by its manufacturer with a unique serial number. This serial number can be embedded in any communications from the relay box 200 to uniquely identify the unit.

The relay box insert 206 is provided with a three axis accelerometer. This device can be used for several purposes. An accelerometer can detect physical shocks to the relay box 200 such may be encountered when somebody attempts to defeat the system by striking it to render it inoperable. The accelerometer can also be used to detect vehicle motion, and thus provides a means of detecting if the vehicle is moving despite them not having been a successful breath test.

Figure 10:
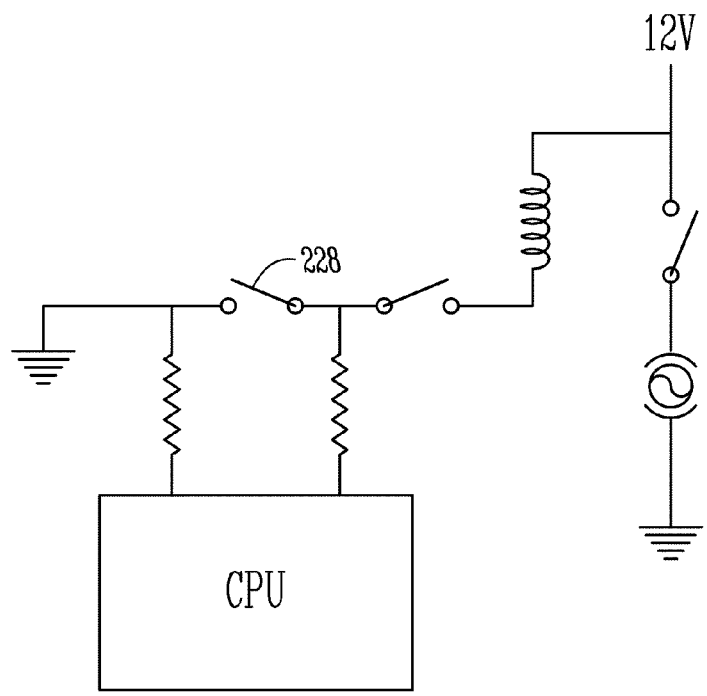
FIG. 10 is a simplified schematic of an electrical circuit used to interlock an ignition according to one embodiment of the present invention.
Figure 13:
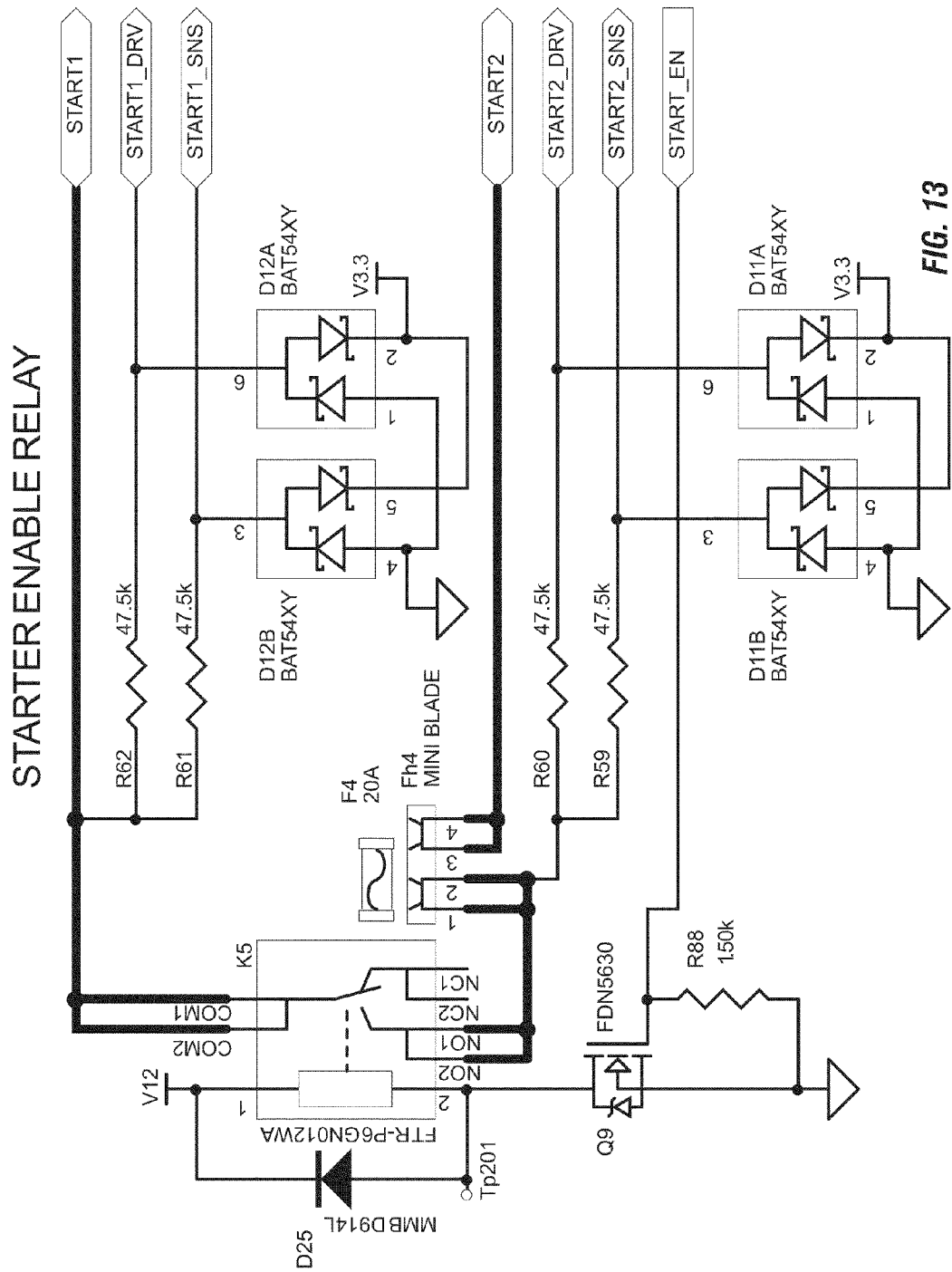
FIG. 13 is a detailed circuit diagram of a starter enable relay according to the present invention.

A number of relays are provided on the power circuit board 210 to allow the relay box 200 to disable the vehicle from starting, or to communicate that it is being operated after the driver has failed a re-test once it has been started. FIG. 10 illustrates a simplified circuit illustrating operation of one such relay. The relay 228 is placed in series with a vehicle control signal such as the starter solenoid power. The relay 228 is connected to the vehicle via two pins on the vehicle interface connector 212, one for each side of the brake made in the ignition control circuit. If an operator attempts to start the vehicle by closing the ignition switch, the relay box computer 230 senses the attempt. If a successful breath test has occurred, the CPU will close the relay 228 to complete the circuit and permit the vehicle to be started. In this fashion, any attempt to short circuit the relay 228 will also be detected, because it will be recorded as an attempt to start the vehicle without a successful breath test. A similar circuit to that shown in FIG. 10 may be provided for the fuel pump as opposed to, or in addition to, the starter circuit. A detailed example of a starter enable relay is shown in FIG. 13.

Figure 11:
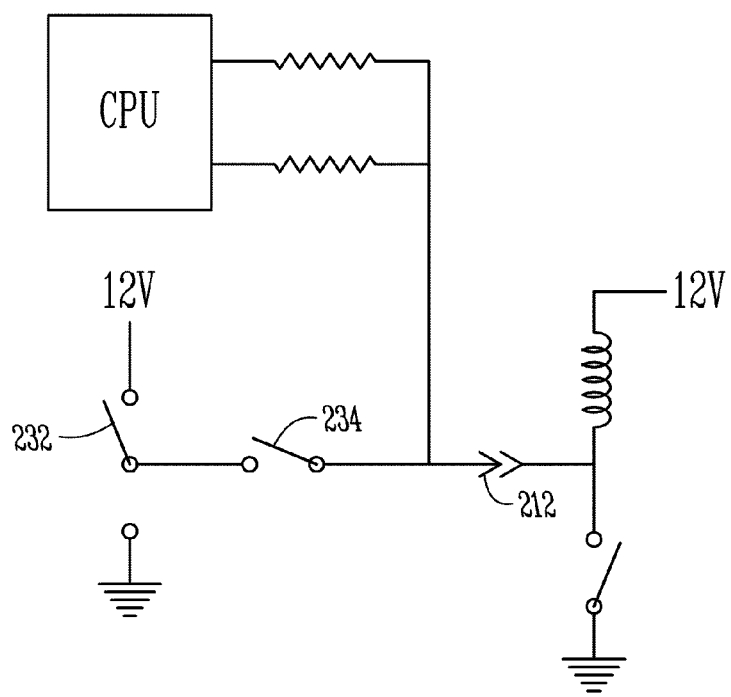
FIG. 11 is a simplified schematic of an electrical circuit that senses the polarity of a vehicle's lights according to one embodiment of the present invention.
Figure 14:
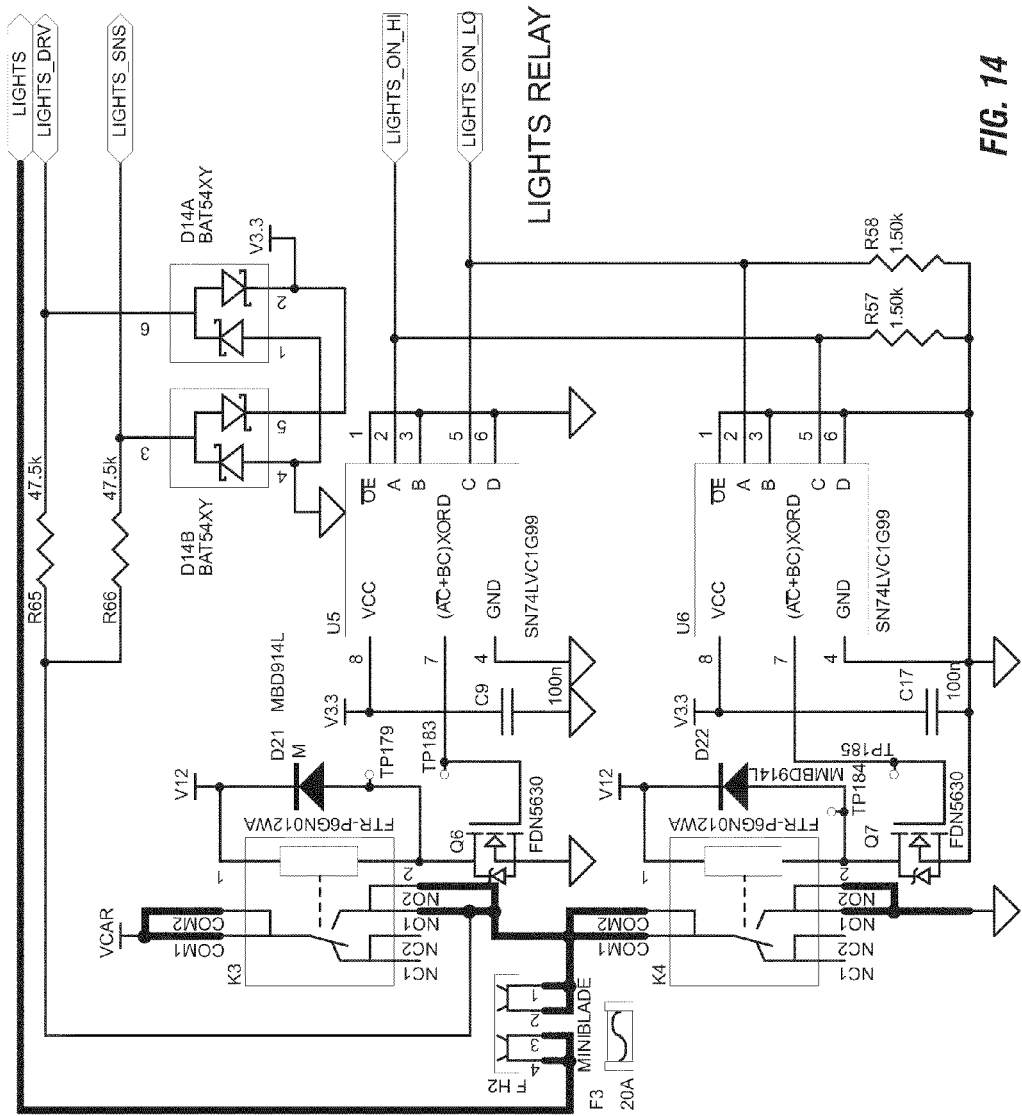
FIG. 14 is a detailed circuit diagram of a lights relay according to one embodiment of the present invention.

Additional relays may be provided to control other vehicle functions. These relay outputs are intended to be wired in parallel with an existing vehicle control wire, such as the power to the horn or the parking lights. A simplified circuit diagram illustrating this feature is shown in FIG. 11. Two relays may be provided to provide such control. A first relay 232 to select either a high (typically 12 V) or low voltage (typically ground) to activate the function, and a second relay 234 to either send or not send the selected voltage to a single pin on the vehicle interface connector 212. This configuration permits either the relay box or the intended vehicle switch to activate the function, and the relay box will not lock out the function. A detailed circuit diagram of the lights relay is shown in FIG. 14. The typical usage of these controls would be to honk the horn or flash the parking lights in order to draw attention to the vehicle in case it has been started without a successful breath test, or in case of failure of a rolling breath test. In jurisdictions which forbid either of these actions, a failure of a rolling re-test might result in an audible warning similar to that emitted by a smoke detector within the confines of the vehicle to discourage use of the vehicle in the event of a failed re-test.

The computer is able to assess the state of each relay 10 of the vehicle interface connector 212 at any time, regardless of the state of the relay. It is also able to stimulate each pin through a high resistance which does not allow activation of a vehicle function connected to the pin. These capabilities allow the computer to learn the expected responses of each pin that is connected to the vehicle at the time the unit is installed. The relay 232 is adjusted automatically by the CPU to be connected to the appropriate voltage (typically either ground or 12 V). Each time a test is performed, or an output changed, the computer can sense the state of the various pins and detect any anomalies. The system is able to detect if a different wire has been disconnected from the relay box, or if a pin has been shorted to another pin or external voltage source. Upon detection of an anomalous condition, the event is logged as a tamper event in the flash memory, and can be reported to the service provider via the cellular phone data link. This is also important because it permits simplified installation of the system. For example, in some vehicles the ignition switch may be provided between the high voltage in the starter, rather than between the starter and the ground.

Additionally, the vehicle interface connector 212 receives a signal that indicates the status of the engine tachometer. In conjunction with the ignition switch circuitry, the tachometer signal can be used to determine if the vehicle is being driven and whether rolling re-tests should be conducted.

External Camera

Figure 12:
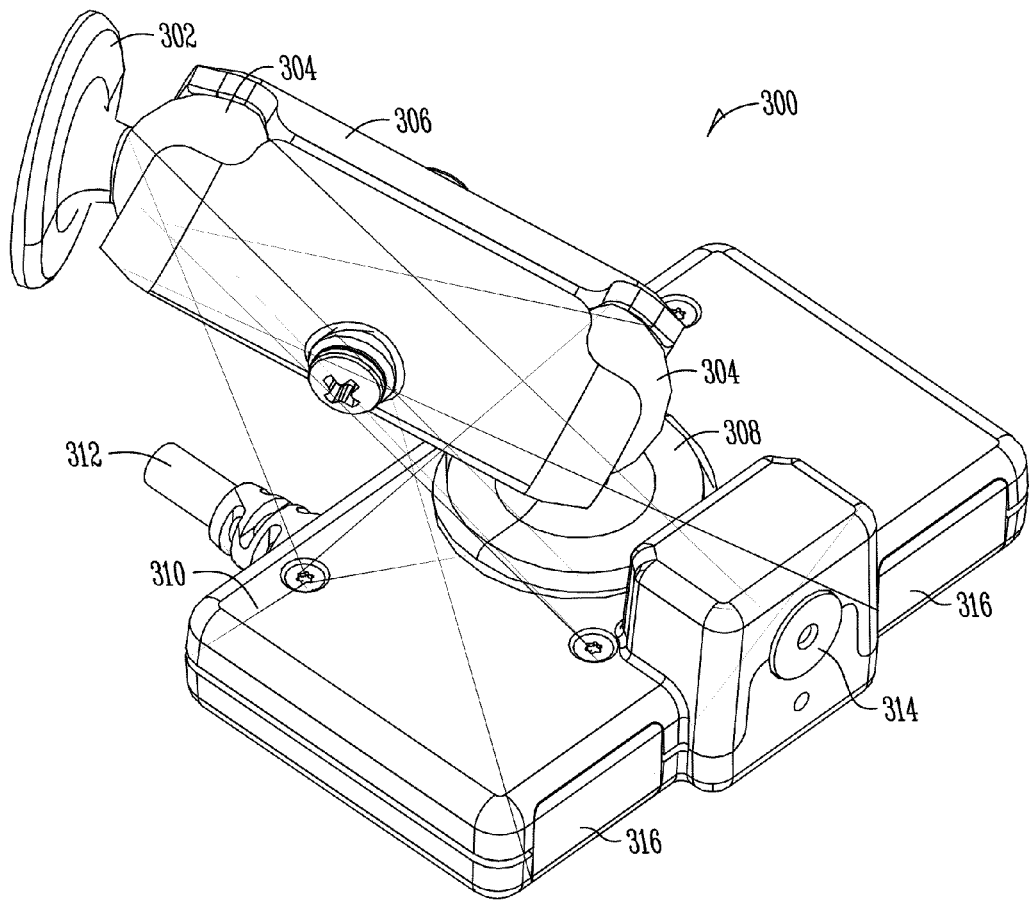
FIG. 12 is a perspective view of an external camera unit for verifying that the person providing the breath sample is the driver according to one embodiment of the present invention.

FIG. 12 shows camera unit 300 that may be attached to an internal surface of the vehicle, such as the windshield or dashboard. A mounting base 302 may include a flat surface or a suction cup with a ball joint 304 that attaches to an extension 306. An attachment base 308 is connected at the opposite end of the extension 306. The attachment base 308 is attached to a camera body 310, so that the camera body 310 is attached to the mounting base 302 to allow it to swivel for selectively aligning the camera body 310 within the vehicle to point in a desired direction. The camera body 310 has a cord 312 that may be connected to the relay or to a power source. A camera 314 is provided in the camera body 310 for recording images of possible drivers as they provide a breath sample. Preferably the camera 314 will record images in both the visible spectrum and the infrared (IR) spectrum. IR light emitting diodes (LEDs) 316 are provided in the camera base 308 to provide IR illumination of a possible driver as the camera 314 captures a digital image of the possible driver. IR illumination is preferable to standard flash or other bright visible lighting that would be distracting, or worse temporarily blinding, to a driver whose eyes are accustomed to low light. The camera unit 300 may include an internal memory for storing digital files of the images. It may also include structure for downloading the digital files of the images to the relay or to the service provider. The digital image files may be time stamped or otherwise indexed to associate them with a particular breath sample. The image files may be still images or may be short video clips of the breath sample being given.

Use of the System

The structures and features described above and shown in the figures may be used to test possible drivers of a vehicle before and during operation of the vehicle to assure that they are not operating the vehicle in a potentially dangerously intoxicated state. The system 10 includes numerous features that can detect and thwart attempts to bypass or defeat the breath test interlock.

With reference to FIGS. 1 and 2, a user (possible driver) 30 that desires to operate the vehicle 20, must first provide an acceptable breath sample to the breathalyzer ignition interlock device 10. The vehicle 20 includes a relay box 200 in connection with an electrical system of the vehicle 20 to impede operation of the vehicle 20 unless and until an acceptable breath sample is provided to the hand held testing unit 100. The driver 30 uses the keypad 112 to activate the handheld unit 100. A display on the screen 108 indicates when the device 100 is ready for use, and may display brief instructions on its use. The light sensor 110 will automatically adjust the brightness of the screen 108 to an appropriate level based on the ambient lighting conditions. It may take a few moments for the handheld unit 100 to determine whether the included fuel cell 402 (see FIGS. 6 and 7) is at the appropriate temperature of conducting a test. The internal heater 414 (FIG. 6) may be activated to warm the fuel cell to a needed temperature. Once the handheld device indicates that it is ready, the user 30 may provide a breath sample.

To provide a breath sample, a user 30 grasps the handheld unit 100 and places the blow tube 106 in his or her mouth. The camera cover 116 that covers the breath tube camera 146 (FIG. 5) should be oriented directly above the blow tube 106 and pointed directly at the face of the user 30. The user 30 should take a deep breath and blow into the blow tube 106 to provide a breath sample. The pressure sensors (see e.g. transducer 156 in FIG. 5) detect the airflow and make sure that the flow is caused by a blowing action rather than a sucking action on the exhaust tube 118 (FIG. 3). A temperature sensing element provided in the breath stream (see temperature sensor passage 160 in FIG. 6) provides a reading that permits the unit 100 to determine if the sample is at a temperature appropriate to having come from a human lung. The measured pressures allow the rate of flow, and ultimately the sample volume to be determined. The sample volume must be sufficient to have used air from the deep portion of the lung where the breath alcohol content is proportional to that of the user's blood.

As the user 30 provides the breath sample by blowing into the blow tube 106, the blow tube camera (image recorder) 146 records a digital image of the user 30 and the second camera 150 records and image that verifies the location of the handheld unit 100. For example, the steering wheel of the vehicle 20 may have a special target or sticker that can be recognized by the computer when captured as an image from the proper distance and alignment. Preferably the sticker would be tamper proof and would be printed with permanent ink that is reflective of IR wavelength. Alternatively, it may be possible to use recognition software that would permit recognition of the steering wheel, or some other internal component of the vehicle 20. If the verification image is not recognized, the test would be considered not acceptable. In another embodiment the verification image is recorded and logged with the test results and the test subject image, but there is no pre-recognition required for an acceptable test that permits starting of the vehicle 20. The handheld unit 100 may give an audio message or a message on the display indicating that a re-test is necessary. The handheld unit 100 may give an audio indication when the verification image is recognized so that the user 30 knows that it is acceptable to proceed with the test.

As best illustrated in FIGS. 6 and 7, during the initial phase as the user is blowing into the blow tube, the breath is simply allowed to flow into the inlet tube 148 and out the exhaust tube 118. During this initial phase the valve 404 is set such that the inlet 422 to the fuel cell 402 is closed. Once a sample has met the criteria of pressure, temperature, flow rate and volume, the valve 404 is adjusted to connect the sample inlet 158 with the fuel cell inlet 422, and the pump 406 provides a slight positive pressure to the fuel cell outlet 426. The pump 406 then reverses and provides a vacuum at the fuel cell outlet 426 to induce a portion of the sample from the exhaust tube 118 through sample inlet 158 into an alcohol-specific fuel cell 402. The pump 406 is precisely controlled to move a repeatable volume of sample into the cell 402 for each test. Preferably the pump 406 will be set to withdraw the sample smoothly so that the flow of sample through the fuel cell weirs 424 is smooth and even. The sample portion will interact with the electrode 428 to create a measurable current that corresponds with the alcohol content of the sample portion. The outlet wires 412 transmit the measured current to a computer processor within the handheld unit 100 that translates the voltage into an estimated blood alcohol content for the user. The test results will be transmitted to the relay 200 where they will be recorded into a log and either immediately or at a later time re-transmitted to a service provider 40. The test results may be displayed on the handheld unit display 108.

If the estimated blood alcohol content is above an acceptable level, the relay 200 will not complete the ignition circuit (or in some instances the fuel pump circuit) (see FIG. 10) and the user 30 will not be able to start the vehicle 20. The failed test will be recorded and logged in the memory of the relay computer, and the results will be communicated to the service provider 40 by the cellular phone. The identity of the person providing the unacceptable test may be determined by review of the associated digital image that was captured while the sample was being provided. The system 10 may lock out starting of the car for some time period after a failed test. The display 108 of the handheld unit 100 may indicate the time remaining before another test may be attempted, or may provide other information regarding the reason the test was not acceptable.

If the estimated blood alcohol content is at an acceptable level, the user 30 may start the vehicle 20. The relay 200 will complete the ignition circuit for the starter (see FIG. 10) and the user 30 will be able to operate the vehicle 20. After a short interval (sometimes a few minutes, sometimes a randomly selected time interval), a re-test may be required. This is sometimes referred to as a "rolling re-test" as it occurs after the car 20 has started; however, for safety reasons it is recommended that the user pull over to a safe location and conduct the test with the car in park. The re-test will transpire in much the same fashion as the initial test. It will be possible to compare the images of the persons that performed the tests to verify that the same person performed both tests.

If an unacceptable sample is given during a re-test, after the vehicle 20 is started, the violation will be recorded and logged and transmitted to the service provider 40 by cellular phone. Service provider 40 may be able to communicate with the driver 30 either by sending messages to the handheld via cell phone that are transmitted to the handheld by Bluetooth link, or possibly by live communication via cellular phone. The location of the vehicle may be determined from the GPS coordinates provided by the GPS unit within the relay 200. The service provider 40 may contact authorities in the vicinity of the vehicle 20 so that the authorities can take action to stop the dangerous situation. The relay 200 may also activate vehicle functions to draw attention to the vehicle 20, such as repeated or sustained honking of the horn and flashing of the parking lights. Alternatively, or in addition to the above, in case of failed re-test, an audio annunciator that is mounted externally to the relay box 200 and emits a smoke-alarm-like noise may be sounded to discourage the driver 30 from continuing to operate the vehicle 20.

The GPS system within the relay 200 records the location of the vehicle 20. If the GPS senses that the relay is changing locations, but an acceptable sample has not been provided, this event will be logged and recorded to be considered as a possible violation. Similarly, if the accelerometers in the relay 200 sense significant movement that is indicative of the vehicle 20 travelling, that is recorded and logged and considered to be a violation if it occurs without an acceptable sample having been provided.

Calibration of the unit 10 should be performed periodically to verify that the fuel cell is accurately reading the samples. To accomplish this, the computer in the handheld unit 100 may be programmed to periodically require the user 30 to initiate a calibration before a test can be performed. Alternatively, the computer in the handheld unit may be programmed to periodically self-initiate a calibration test. The calibration test procedure can best be understood with reference to FIGS. 6 and 7 and the accompanying discussion of those figures above. This calibration system eliminates the need to return the unit to the service provider, typically every 60 to 90 days, to be recalibrated. This results in substantial cost savings and eliminates the inconvenience to the customer of returning the vehicle to an installer location periodically. Additionally, the calibration results may be relied upon to verify for evidentiary purposes that a failed test result was accurate, so that failed test results may be relied upon to change terms of a violator's operating privileges.

In-Home Monitoring Device

As used herein, it is understood that the phrase "in-home" is exemplary, and intended to include other fixed locations outside of a vehicle such as work locations, like office buildings, etc. The important point being that it is outside of a vehicle ignition system connection. The unit may have a 12 volt adapter for use in a 12 volt vehicle source.

Figure 15:
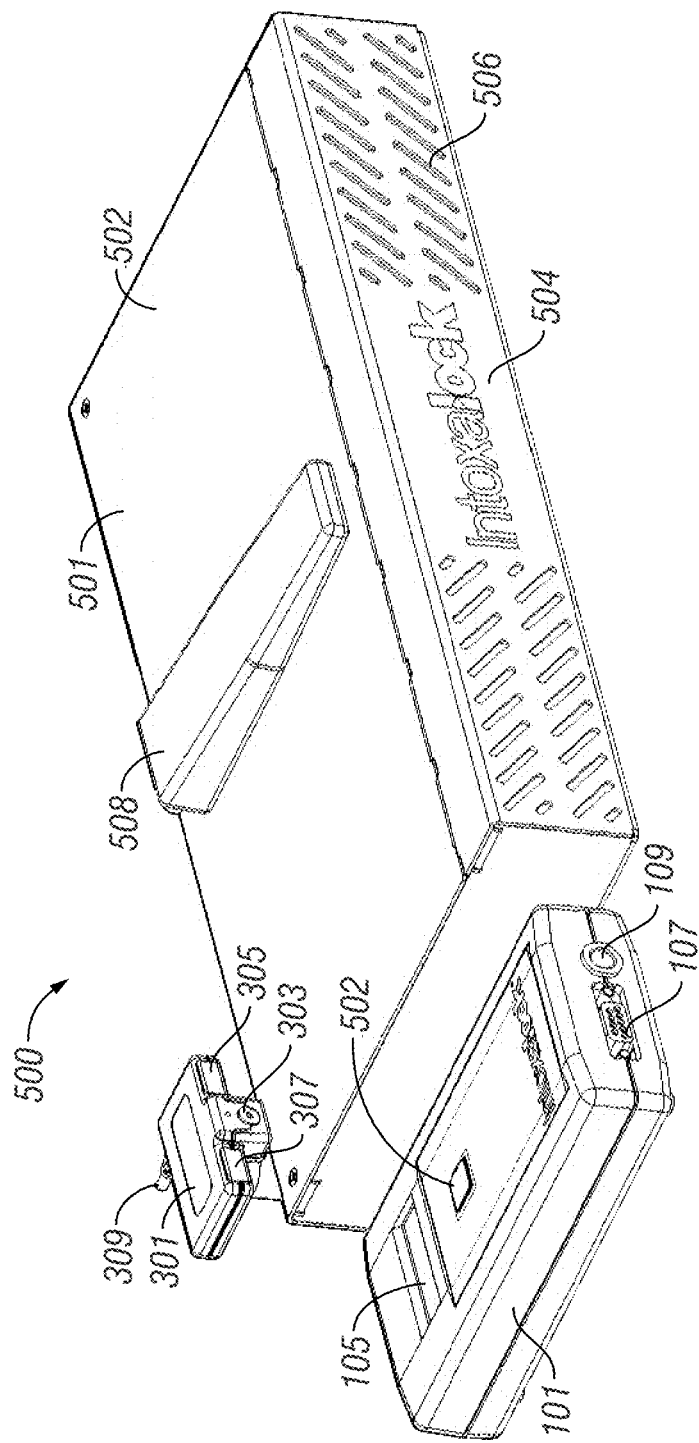
FIG. 15 is an isometric front view of a breath alcohol testing system according to another embodiment of the present invention.
Figure 16:
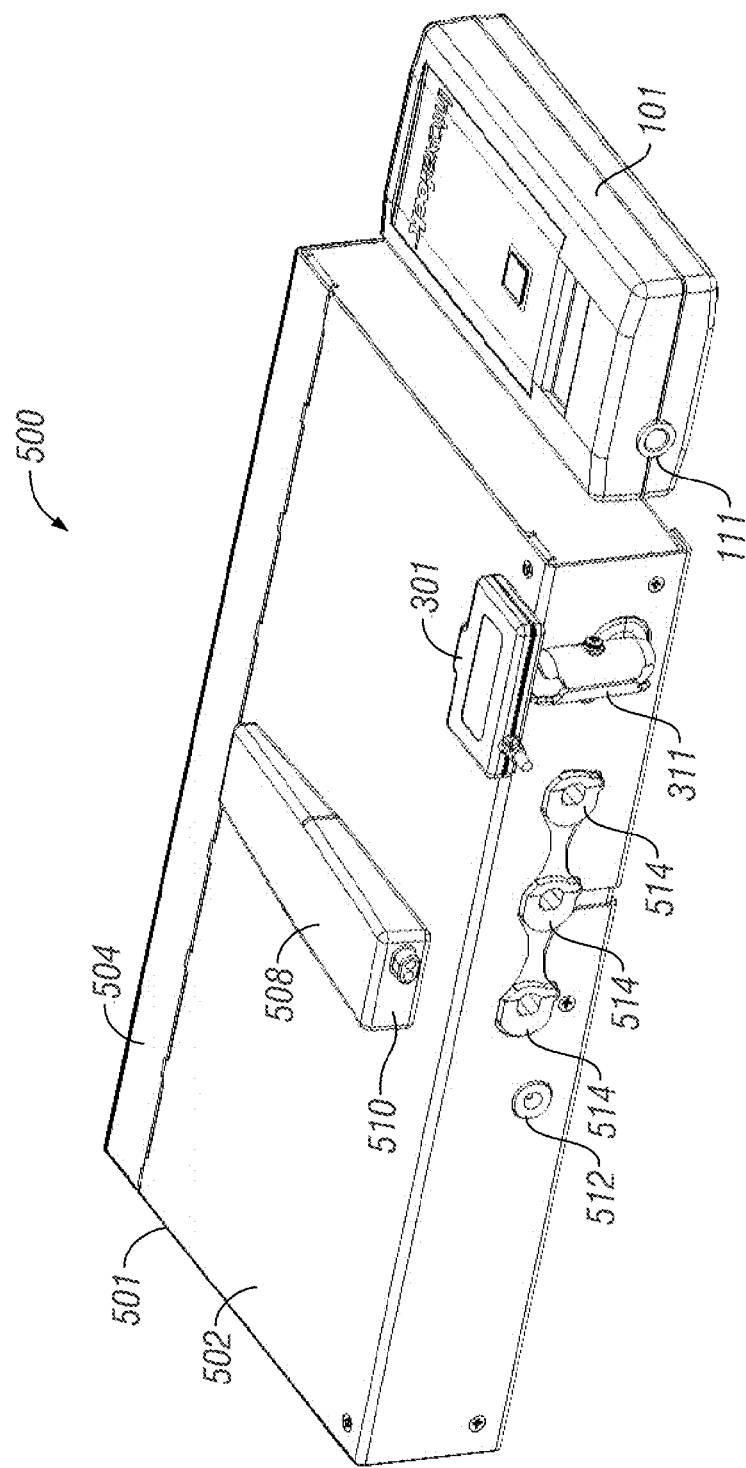
FIG. 16 is an isometric rear view of the breath alcohol testing system of FIG. 15.

FIGS. 15 and 16 show a monitoring apparatus 500 that is intended for in-home use by a person that needs to periodically provide a breath sample. The apparatus 500 is intended to be somewhat portable such that a person who is required to give periodic breath samples may take and use the apparatus 500 at different locations and apart from any vehicle. Most commonly this might be used in the home of a person who is on probation or under house arrest. However, while it may be referred to herein as an "in-home" apparatus or system, its use is naturally not limited to use within a home.

The monitoring system 500 includes a base unit 501 and a handheld breath alcohol testing device 101. The handheld testing device 101 may be of the same design as the handheld unit 100 described in detail above and shown in FIGS. 2-5. Other known designs for a handheld testing device 101 may also be utilized. In the handheld testing device 101 shown in FIGS. 15 and 16, the device 101 includes a power button 103, a display screen 105, a nine-pin connector 107, a breath inlet 109 for connection to a breath tube (not shown, but see FIG. 2), and a breath exhaust 111. The handheld device 101 must be capable of receiving a breath sample, testing that sample's alcohol content, and electronically communicating the test results. Those of skill in the art will be aware of various designs for the handheld testing device 101 that can be used advantageously within the in-home monitoring system 500 of the present invention.

An image recorder, such as digital camera 301 is preferably provided as part of the monitoring apparatus 500. The digital camera 301 may be of the same or similar design to camera unit 300 described above and shown in FIG. 12. The image capturing device may be capable to capturing still or video images. As best seen in FIG. 16, the camera 301 may be advantageously mounted to the base unit 501 on a swivel mount 311. A power and data cord 309 can be provided to power the camera 301 and provide a path for transferring image data to the base unit 501. The camera 301 shown includes light emitting diodes 305 and 307, which may be standard or IR emitting diodes. A lens 303 is provided to focus and capture an image of video of a person giving a breath sample. In use, the swivel mount 311 permits the camera 301 to be adjusted so that the lens points at the user. The camera 301 may include an internal memory for storing digital files of the images. The digital image files may be time stamped or otherwise indexed to associate them with a particular breath sample. The image files may be still images or may be video clips of the breath sample being given.

With continued reference to FIGS. 15 and 16, the base unit 501 has a sealed case formed from various structural members that prevent unauthorized access to internal components of the apparatus 500. The case includes a top cover 502 that generally covers the top of the unit and is affixed to the other structural members of the case by fasteners or screws at the rear and top of the unit 501. The base unit 501 should include tamper resistant features, such as frangible seals that indicate if the top cover 502 has been removed. Hall effect, or similar, sensors may alternatively be provided to provide a signal that the top cover 502 has been removed. This may trigger an immediate alert to a service provider that the unit 501 has been tampered with. A front cover 504 may include vent openings 506 to facilitate heat removal from the internal components. An antenna 508 may be provided to facilitate the apparatus 500 communicating with a remove service provider as will be described in more detail below. The antenna 508 will include a cord (not shown) that connects the antenna 508 with internal components. The antenna 508 may include a cellular phone antenna and a GPS receiver. The antenna 508 may be mounted to the base unit 501, or, more preferably may be loose such that the antenna 508 can be maneuvered and situated slightly apart from the base unit 501 to be located for best receiving and transmitting data. In the case where the antenna 508 includes a GPS receiver, the antenna will preferably be situated near a south facing (in the northern hemisphere) window to facilitate receiving GPS satellite signals.

As best seen in FIG. 16, the rear of the base unit 501 includes input jacks 514 for quick connection to the various external components, namely, the handheld device 101, the camera 301, and the antenna 508. A power jack 512 is also provided at the rear of the unit 501. The power jack 512 may be selectively connected to a power cord (not shown) that is connected to an external power source such as a standard wall AC outlet or a "cigarette light" type outlet. The power jack 512 is adapted to receive DC current, so if connected to an AC source, the power cord must include a rectifier to transform the AC current to DC power.

Preferably the handheld device 101 will include the same tamper resistant features described above such that additional data is also communicated by the handheld device 101. For example, the handheld device 101 should preferably detect, record, and communicate attempts to use anything other than unfiltered human breath to provide the required samples. The handheld device 101 may include an accelerometer to detect, record, and report any attempts to destroy or damage the unit and may include an optional compass to detect movement. The handheld device 101 may include sensors or switches to sense if the cover has been removed.

Figure 17:
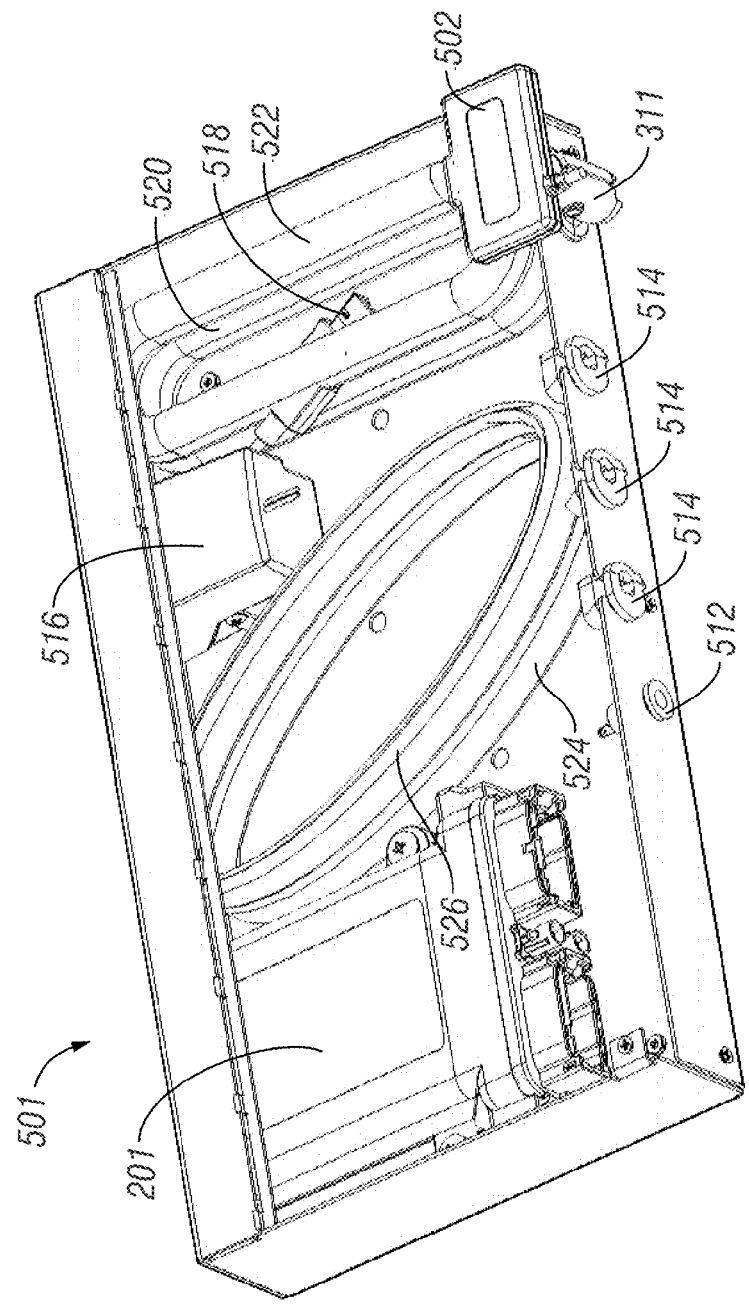
FIG. 17 is an isometric top and rear view of the base unit of the breath alcohol testing system of FIG. 15 with its top cover removed.
Figure 19:
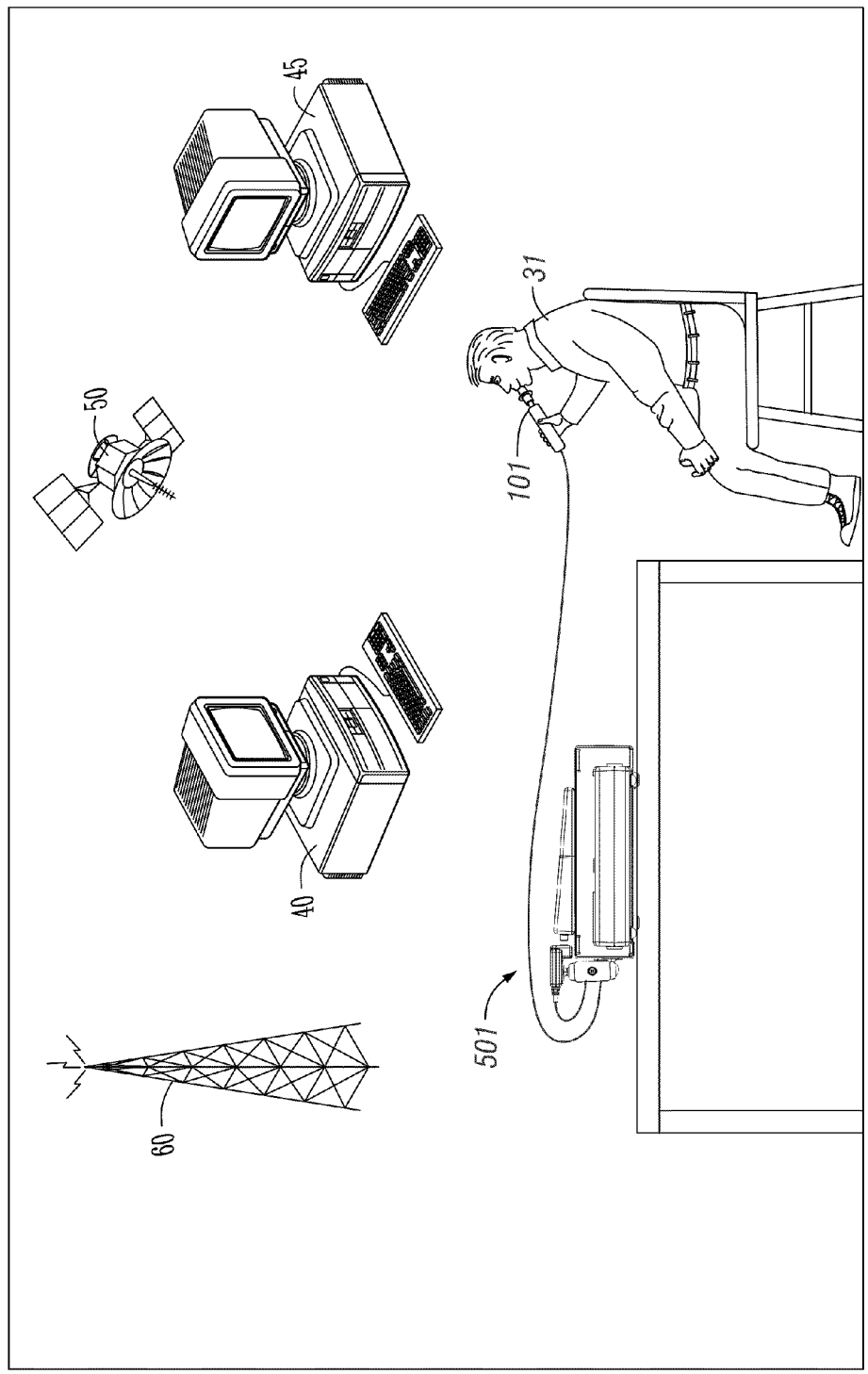
FIG. 19 is a schematic showing a system for administering a breath alcohol testing program that utilizes an ignition interlock device.

FIG. 17 shows the monitoring unit 501 with its top cover removed to reveal the internal components. The internal wiring has been omitted from the figure to aid in clarity. A relay unit 201, of similar to design and functionality to the relay box 200 described in detail above and shown in FIGS. 8 and 9 is mounted within the unit 501. In addition to the relay unit 201, a speaker 516 is provided within the unit 501 to provide audio feedback to a user. A USB connection 518 is provided to provide input to the speaker 516 from the relay unit 201. The camera cable 520, antenna cable 522, USB speaker cable 524, and power cable 526 are shown to indicate generally where they can be coiled within the unit 501. The relay unit 201 generally interconnects and controls the various components, and interfaces with the service provider as will be described in more detail below. The relay unit will necessarily include an electronic storage medium as part of an embedded computer system (microprocessor not shown) to manage the functioning of the monitoring unit 501. The computer system may implement a file storage system in a non-volatile/memory to log test results, tampering events, calibration information, and other pertinent system information FIG. 19 shows a system for administering an in-home breath alcohol testing program according to one embodiment of the present invention. The system is especially well-suited for use by users 31 that are required to provide breath samples to establish that the absence of alcohol from their system even in situations where they will not be operating a motor vehicle. The base unit 501 is placed in a convenient location and a user 31 positions themselves such that the camera 301 is aimed at their face. They provide a breath sample according to the requirements their particular handheld unit 101. The results of test are recorded by the relay unit within the base unit 501 in a manner described above. The relay unit within the base unit 501 also receives the GPS coordinates from satellites 50, and associates the GPS coordinates with the test results. The base unit 501 communicates a log with the test results, GPS data, images, and other associated data to computers 40 at a service provider. The service provider computers 40 are connected to receive and send data from and to the Internet. The communication between the base unit 501 and the service provider computers 40 may occur, for example, from the cellular communication equipment provided in the relay unit via cellular towers 60 that are ultimately in communication with servers connected to the Internet. Alternatively, the in-home base unit 501 may be hardwired to an Internet connection in order to communicate the data files to the service provider computers 40.

Figure 18:
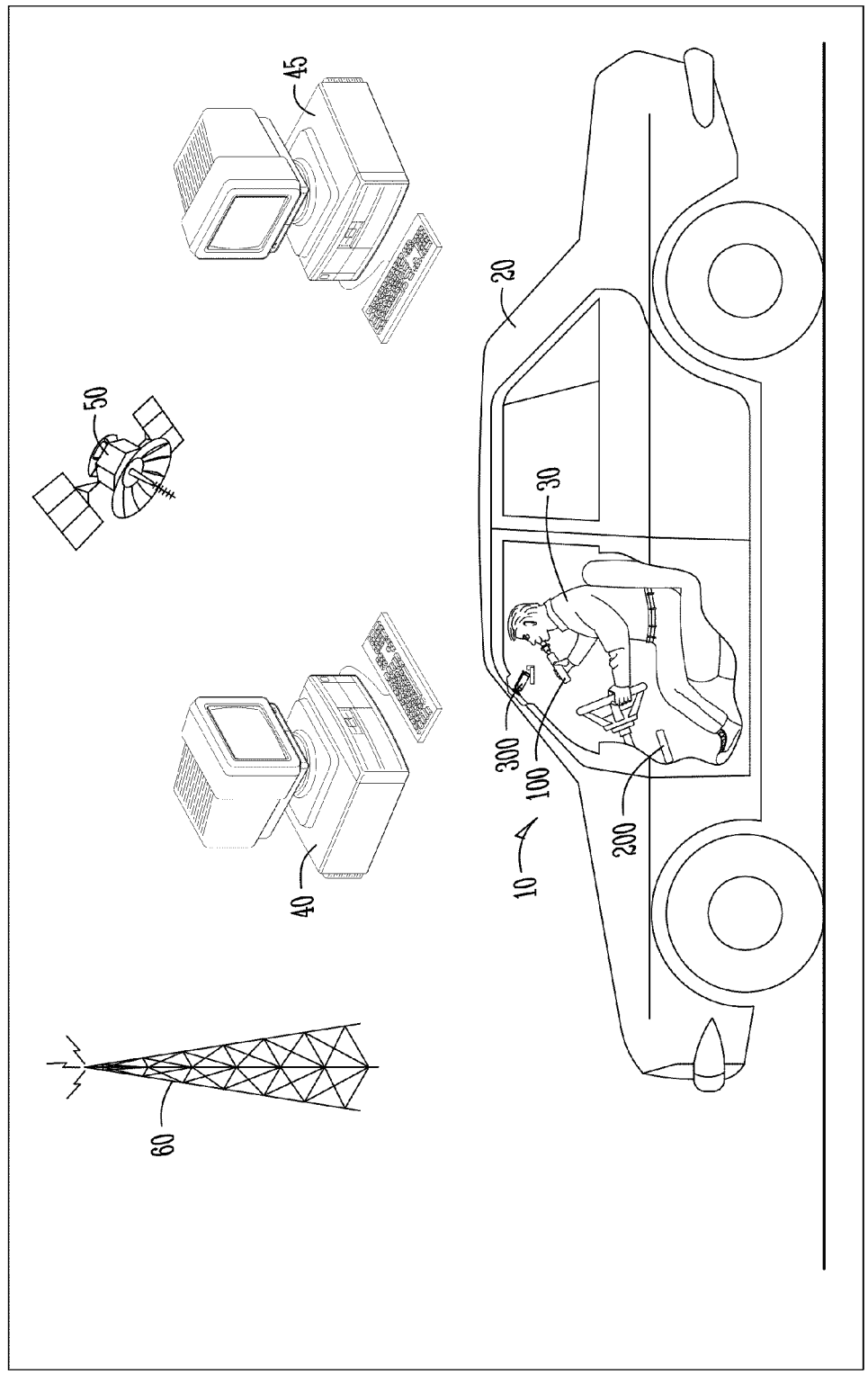
FIG. 18 is a schematic showing a system for administering an in-home breath alcohol testing program.

FIG. 18 shows a system for administering a breath alcohol testing program that utilizes an ignition interlock according to one embodiment of the present invention. The system of FIG. 18 is quite similar that shown in FIG. 19. The results of test are recorded by the relay unit 200 in a manner described above. The relay unit 200 also receives the GPS coordinates from satellites 50, and associates the GPS coordinates with the test results. The relay 200 communicates a log with the test results, GPS data, and other associated data to computers 40 at a service provider. The service provider computers 40 are connected to receive and send data from and to the Internet.

The service provider computers 40, which in practice may be more than one computer linked to operate as a computer system, of both FIGS. 18 and 19 are programmed to manipulate and react to the data received from the base unit 501 or relay 200. The service provider computers 40 can be programmed to implement various protocols established by any monitoring authority. The monitoring authority might be law enforcement, correctional authorities, or state departments of transportation. Alternatively, the monitoring authority might be a civil organization such as a trucking company that monitors the drivers of its fleet of trucks. The service provider computers 40 can be programmed to implement a variety of protocols established by numerous monitoring authorities.

For example, the computers 40 may create log tables that can be viewed via the Internet or other computer network by remote monitoring authority computers 45. Viewing access to the log tables may be controlled by password or other known protections. The remote monitoring authority computers 45 might be computers operated and monitored by law enforcement or correctional authorities. Alternatively, the monitoring authority might be a civil organization such as a trucking company that monitors the drivers of its fleet of trucks. The log tables might include in tabular form information about all of the tests of a particular user over a period of time. The information could include the date, time, and location of the test, and an indication of whether the test was successful or failed. The information in the viewable log might also include an image that was captured when the breath sample was provided. Alternatively, the table might include a link to an image or video of the sample being provided. It has been found that when a user is aware that an image or video of the user providing the sample will be provided to the monitoring authority, especially in real time, or nearly real time, this knowledge is a powerful incentive not to attempt to thwart the system. Furthermore, including the image may permit a monitoring authority to determine whether the image data is consistent with the geographic information If the test was failed, an indication of what triggered the failure categorization can be included in the viewable log. Examples of reasons for failure might include: presence of alcohol in the breath sample, failure to provide a sample, unacceptable temperature, unacceptable GPS coordinates for test location, interruption of power, and any indication of tampering with the case. Other information indicative of attempts as thwarting the system may also be provided. Any failed test may be visually highlighted so it is apparent at a glance to the monitoring authority if a user has had a failed test. The user might also be provided with access to the log tables so they can monitor their own results.

In addition to providing passive feedback to monitoring authority computer 45, the provider computers 40 may be programmed and adapted to trigger affirmative steps in response to a failed test. The monitoring authority may wish to only have the violation noted in the viewable log for minor violations; whereas major violations, or violations that implicate the public health may be appropriate for receiving an immediate alert such as an e-mail, text message, automatically generated telephone call, or the like. For example, if a breath test indicates the presence of alcohol, but only in trace amounts, it might be sufficient to only note the violation in the log. However, if the breath test indicates a higher level of alcohol concentration, the monitoring authority may wish to receive immediate notice, so that they can determine whether to take action. In still more dire situations, the computers 40 may be programmed to dial 911 and provide an automated message based on the GPS location from which the sample was provided if the information indicates that a vehicle is being operated by a severely intoxicated driver.

The service provider computers 40 can be adapted to a variety of protocols for different monitoring authorities that are often operating under different laws and regulations. The computers 40 can also be quickly updated to immediately reflect changes in the protocols for the same monitoring authority.

A preferred embodiment of the present invention has been set forth above. It should be understood by one of ordinary skill in the art that modifications may be made in detail, especially in matters of shape, size, and arrangement of parts. Such modifications are deemed to be within the scope of the present invention, which is to be limited only by the broad general meaning of the terms in which the appended claims are expressed.

What is claimed is:

1. An in-home breath alcohol monitoring apparatus comprising:
   a handheld breath alcohol testing device capable of detecting, recording and communicating attempts to use anything other than unfiltered human breath, and capable of receiving a breath sample and testing the breath sample to determine its temperature, induced air pressure and alcohol content;
   an image recorder adapted to record image data when the breath sample is provided;
   a sealed case base unit enclosing an electronic storage medium in communication to receive information regarding the determined alcohol content and the breath sample temperature and pressure, the storage medium being further adapted to receive image data associated with the determined alcohol content; and
   a communication device mounted within the sealed case for transmitting data related to the determined, alcohol content and the associated image data to a remote service provider and transmitting information for creating a viewable log of what triggered failure of a breath alcohol test.

2. The in-home breath alcohol monitoring apparatus of claim 1 wherein the communication device mounted within the sealed case base unit is wireless.

3. The in-home breath alcohol monitoring apparatus of claim 1, wherein the electronic storage medium and the communication device are contained within a relay box mounted inside the sealed case base unit.

4. The in-home breath alcohol monitoring apparatus of claim 3, wherein the relay box includes an accelerometer for determining attempts to tamper with or move the sealed case base unit.

5. The in-home breath alcohol monitoring apparatus of claim 1, wherein the monitoring apparatus includes a compass to detect movement.

6. The in-home breath alcohol monitoring apparatus of claim 1, further comprising a speaker mounted within the sealed case base unit.

7. The in-home breath alcohol monitoring apparatus of claim 1, wherein the sealed case base unit includes a cover, further comprising a mechanism for detecting attempts to remove the cover.

8. The in-home breath alcohol monitoring apparatus of claim 7, wherein the mechanism for detecting attempts to remove the cover comprises a sensor.

9. The in-home breath alcohol monitoring apparatus of claim 8, wherein the any detected attempts to remove the cover are logged on the electronic storage device and communicated to the remote service provider.

10. The in-home breath alcohol monitoring apparatus of claim 7, wherein the mechanism for detecting attempts to remove the cover comprises a frangible element.

11. The in-home breath alcohol monitoring apparatus of claim 1, further comprising a GPS receiver in communication with the electronic storage medium to provide GPS data to the electronic storage medium associated with each breath sample.

12. The in-home breath alcohol monitoring apparatus of claim 11, further comprising an antenna unit including the GPS receiver and an antenna for the communication device, the antenna unit being external to the sealed case base unit.

13. The in-home breath alcohol monitoring apparatus of claim 1, further comprising a mount on an exterior of the sealed case base unit for supporting the image recorder.

14. The in-home breath alcohol monitoring apparatus of claim 1, wherein the sealed case base unit comprises connection sockets for electronically connecting the image recorder with the electronic storage medium, the handheld testing device with the electronic storage medium, and a GPS receiver with the electronic storage medium.

15. The in-home breath alcohol monitoring apparatus of claim 14, wherein the electronic storage medium records instances when any of the image recorder, the handheld testing device, or the GPS receiver have been disconnected from the electronic storage medium.

16. A system for administering an in-home breath alcohol testing program, the system comprising:
- a handheld breath alcohol testing device capable of detecting, recording and communicating attempts to use anything other than unfiltered human breath, and capable of receiving a breath sample and testing the breath sample to determine its temperature, induced air pressure and alcohol content;
- a sealed case base unit enclosing an electronic storage medium in communication with the handheld testing device to receive an indication of the determined alcohol content and the breath sample temperature and pressure;
- a communication device mounted within the sealed case for transmitting data related to the breath alcohol testing and transmitting information for creating a viewable log of what triggered failure of a breath alcohol test; and
- a service provider computer system adapted to receive the data related to the breath alcohol testing.

17. The system of claim 16 wherein the communication device is a wireless communication device.

18. The system for administering an in-home breath alcohol testing program of claim 16, wherein the service provider computer system is adapted to generate a viewable log with information regarding the data related to the determined alcohol content, and wherein the viewable log is stored on the service provider computer system such that it can be viewed via the Internet by a monitoring authority provided with access to the viewable log.

19. The system for administering an in-home breath alcohol testing program of claim 18, wherein the service provider computer system is adapted to recognize when the received data related to the breath alcohol testing indicate that a protocol established by a monitoring authority has been violated and to provide a visual indication within the viewable log of any such violation.

20. The system for administering an in-home breath alcohol testing program of claim 19, wherein the service provider computer system is adapted to generate a message that gets sent to the monitoring authority regarding any such violation.

21. The system for administering an in-home breath alcohol testing program of claim 19, wherein the service provider computer system is adapted to recognize when the received data related to the breath alcohol testing indicate that any of a plurality of protocols established by the monitoring authority has been violated and to provide a visual indication within the viewable log of any such violation; and further wherein the service provider computer is adapted to generate a message that gets sent to the monitoring authority when specified ones of the plurality of protocols are violated.

22. The system for administering an in-home breath alcohol testing program of claim 18, wherein the data related to the breath alcohol testing comprises GPS coordinates of a location where the breath sample was received, and wherein the viewable log includes geographic information regarding the location where the breath sample was received.

23. The system for administering an in-home breath alcohol testing program of claim 22, wherein the service provider computer system is adapted to send a message to the monitoring authority if the GPS coordinates indicate a geographic location that is not acceptable.

24. The system for administering an in-home breath alcohol testing program of claim 18, wherein the data related to the breath alcohol testing comprises image data recorded when the breath sample was received, and wherein the viewable log includes an image created from the image data.

\* \* \* \* \*